(12) United States Patent
Matsunaga et al.

(10) Patent No.: US 12,256,813 B2
(45) Date of Patent: Mar. 25, 2025

(54) BAND DEVICE, WRISTWATCH, AND END PIECE

(71) Applicant: SONY GROUP CORPORATION, Tokyo (JP)

(72) Inventors: Kentaro Matsunaga, Tokyo (JP); Tatsuhito Aono, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 202 days.

(21) Appl. No.: 17/759,197

(22) PCT Filed: Jan. 15, 2021

(86) PCT No.: PCT/JP2021/001222
§ 371 (c)(1),
(2) Date: Jul. 21, 2022

(87) PCT Pub. No.: WO2021/153268
PCT Pub. Date: Aug. 5, 2021

(65) Prior Publication Data
US 2023/0050315 A1    Feb. 16, 2023

(30) Foreign Application Priority Data

Jan. 30, 2020 (JP) ................. 2020-013153

(51) Int. Cl.
*A44C 5/14* (2006.01)
*A44C 5/24* (2006.01)

(52) U.S. Cl.
CPC . *A44C 5/14* (2013.01); *A44C 5/24* (2013.01)

(58) Field of Classification Search
CPC .. A44C 5/14; A44C 5/24; A44C 5/246; A61B 5/681; A61B 5/6824; G04B 37/1486
See application file for complete search history.

(56) References Cited

U.S. PATENT DOCUMENTS

| | | | | |
|---|---|---|---|---|
| 9,833,164 | B2* | 12/2017 | Justice | A61B 5/0533 |
| 10,691,072 | B1* | 6/2020 | Johnson | G04G 9/0064 |
| 11,089,999 | B1* | 8/2021 | Williams | A61B 5/4875 |
| 11,781,907 | B2* | 10/2023 | Capella | G01J 1/0271 |
| | | | | 600/310 |

(Continued)

FOREIGN PATENT DOCUMENTS

| | | |
|---|---|---|
| JP | 50-112195 U | 9/1975 |
| JP | 04-107612 U | 9/1992 |

(Continued)

OTHER PUBLICATIONS

International Search Report and Written Opinion of PCT Application No. PCT/JP2021/001222, issued on Mar. 9, 2021, 14 pages of ISRWO.

*Primary Examiner* — David M Upchurch
(74) *Attorney, Agent, or Firm* — CHIP LAW GROUP

(57) ABSTRACT

A band device according to an aspect of the present disclosure includes a sensor unit, and a band unit that is linked to the sensor unit and forms a hollow part together with the sensor unit. The band unit includes an end piece section to which a watch head section is attached, and an engaging section that makes detachable engagement in a state where the band unit is wrapped around a wrist.

13 Claims, 25 Drawing Sheets

(56) References Cited

U.S. PATENT DOCUMENTS

| | | | | |
|---|---|---|---|---|
| 2016/0070339 A1* | 3/2016 | Crawford | ................ | G06F 3/011 |
| | | | | 345/156 |
| 2020/0329833 A1* | 10/2020 | Matsunaga | .............. | A44C 5/14 |
| 2021/0333759 A1* | 10/2021 | Vasavada | ........... | G04B 37/1486 |

FOREIGN PATENT DOCUMENTS

| | | |
|---|---|---|
| JP | 2015-513066 A | 4/2015 |
| JP | 2015-123371 A | 7/2015 |
| WO | 2019/097779 A1 | 5/2019 |

\* cited by examiner

[ FIG. 1 ]
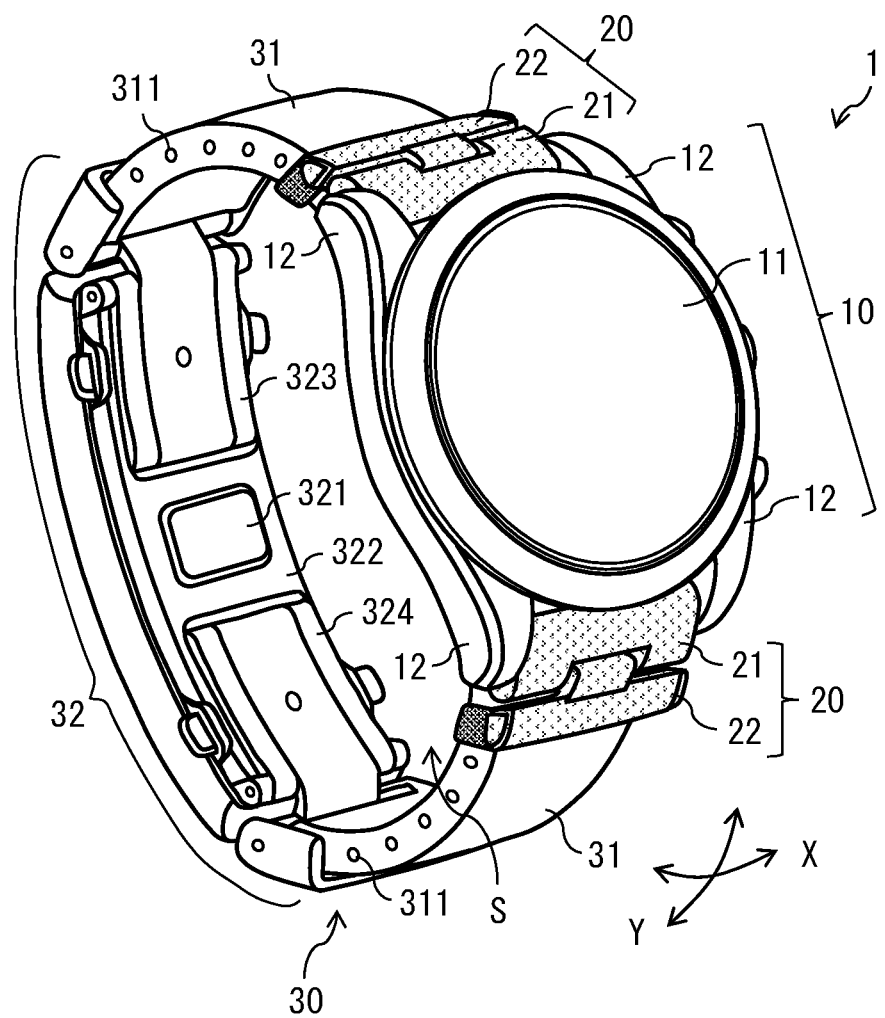

[FIG. 2]
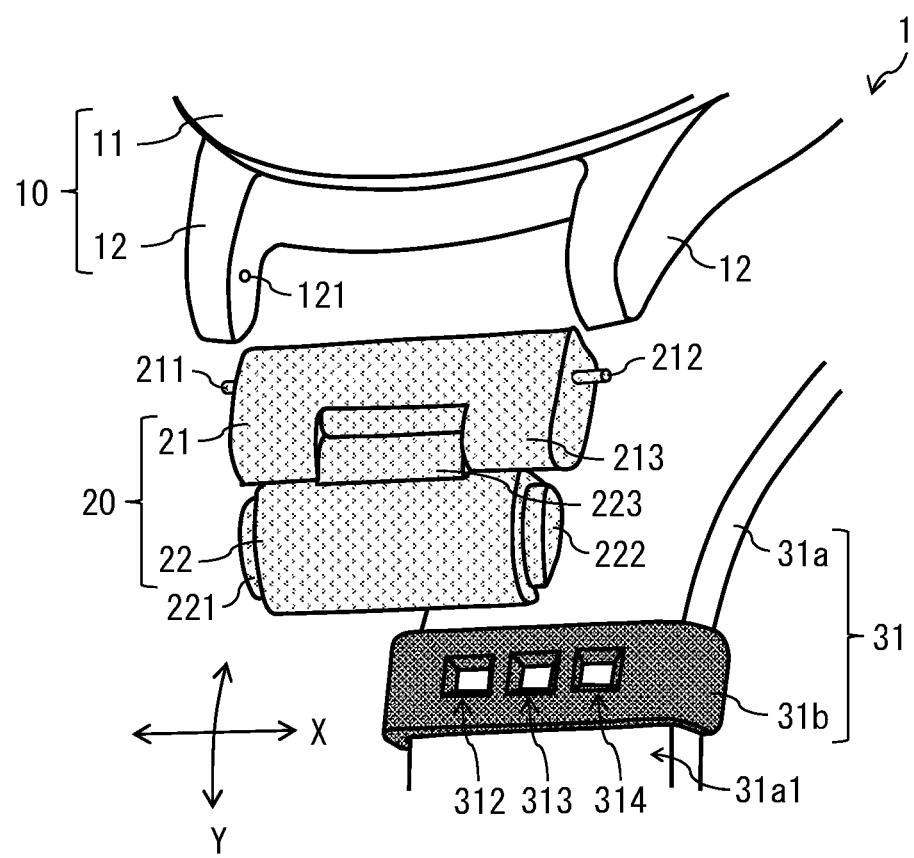

[FIG. 3]
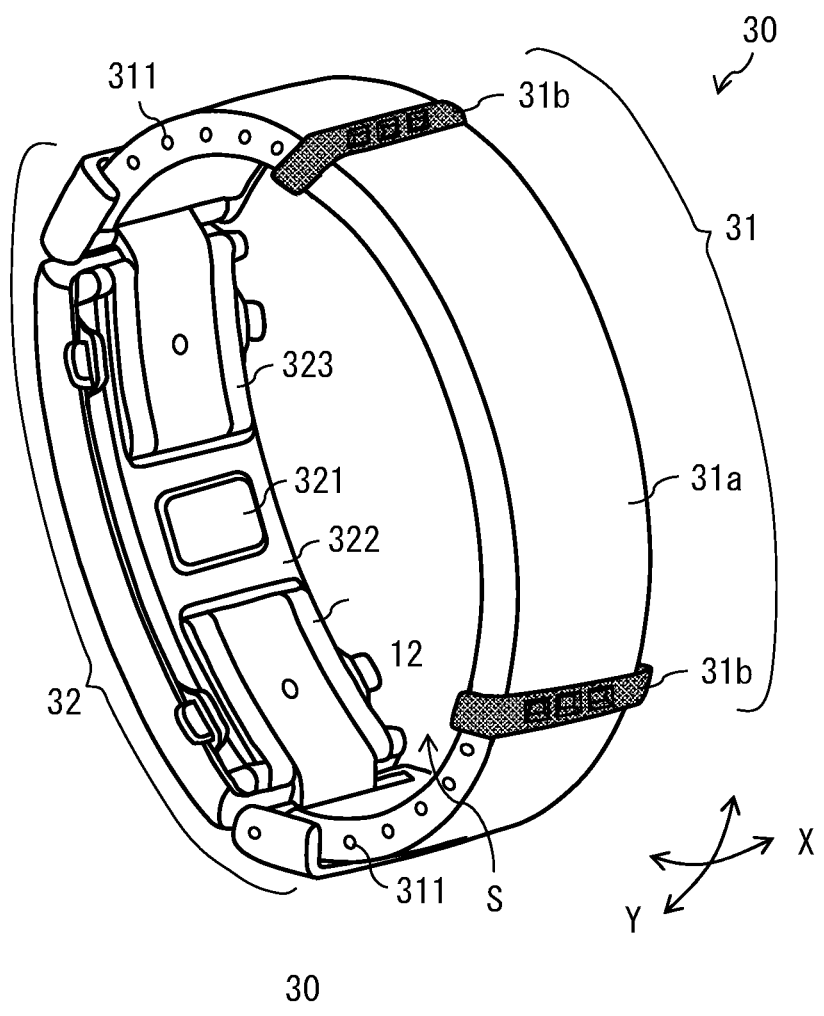

[ FIG. 4 ]
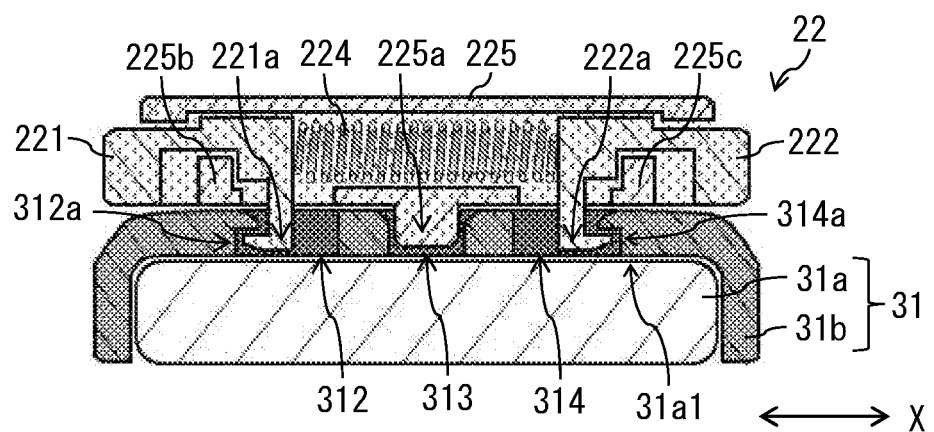
[ FIG. 5 ]
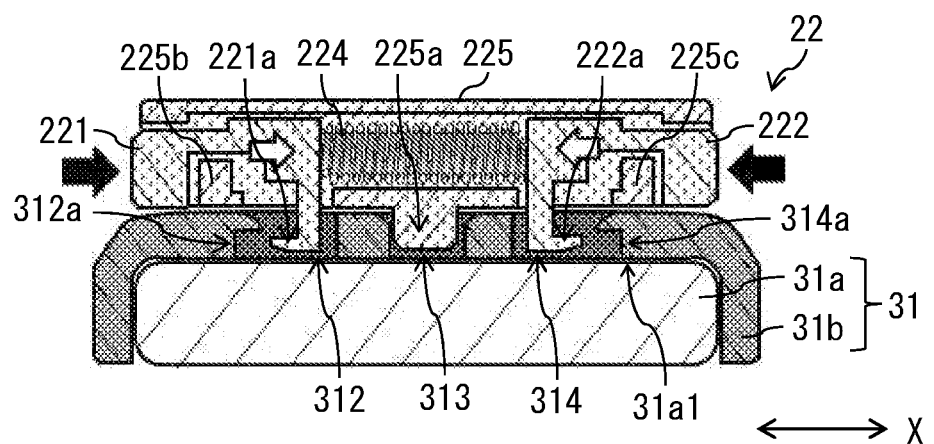

[ FIG. 6 ]
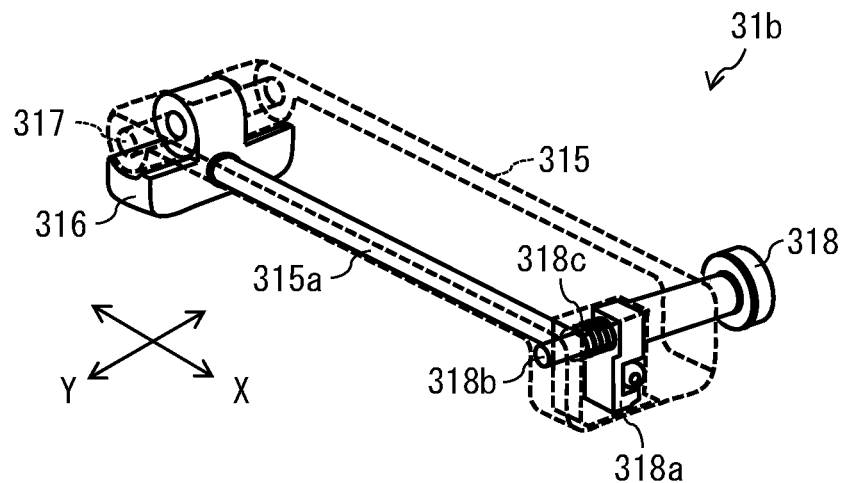
[ FIG. 7 ]
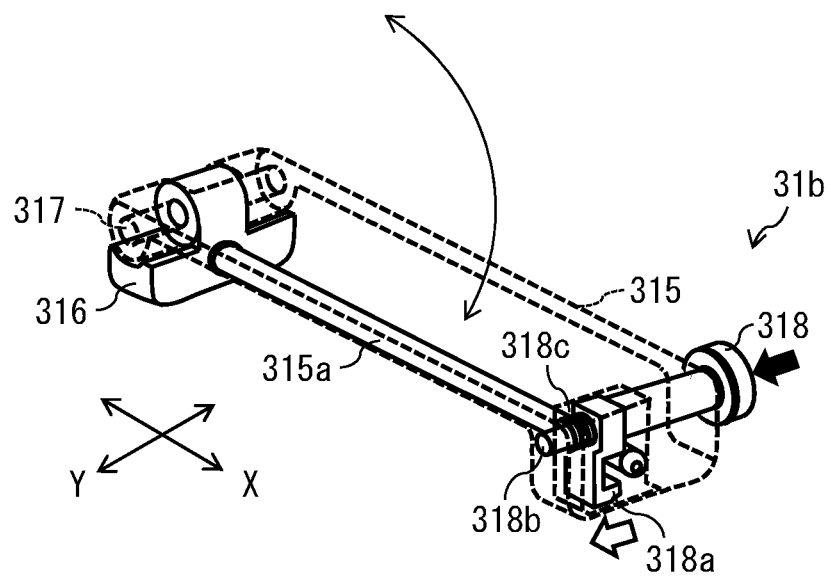

[ FIG. 8 ]
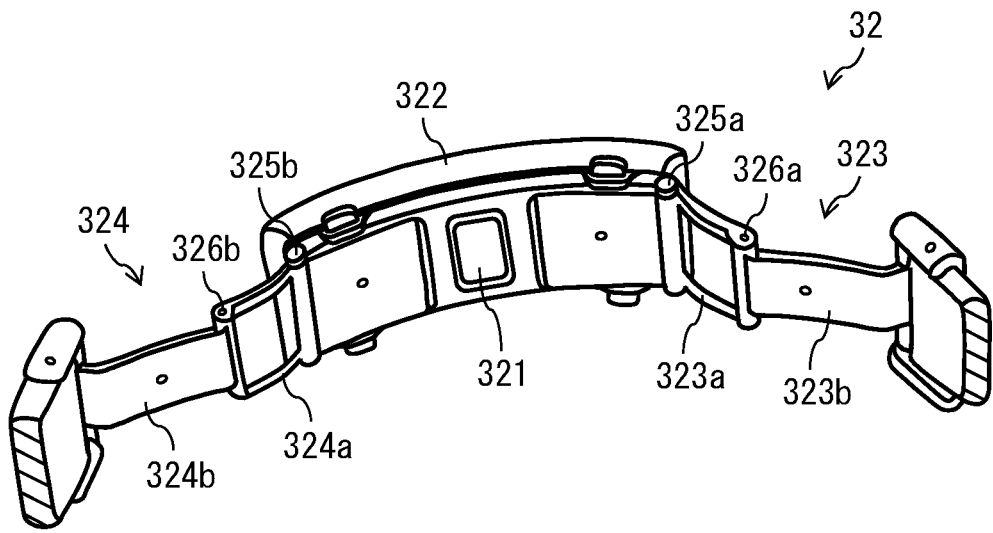
[ FIG. 9 ]
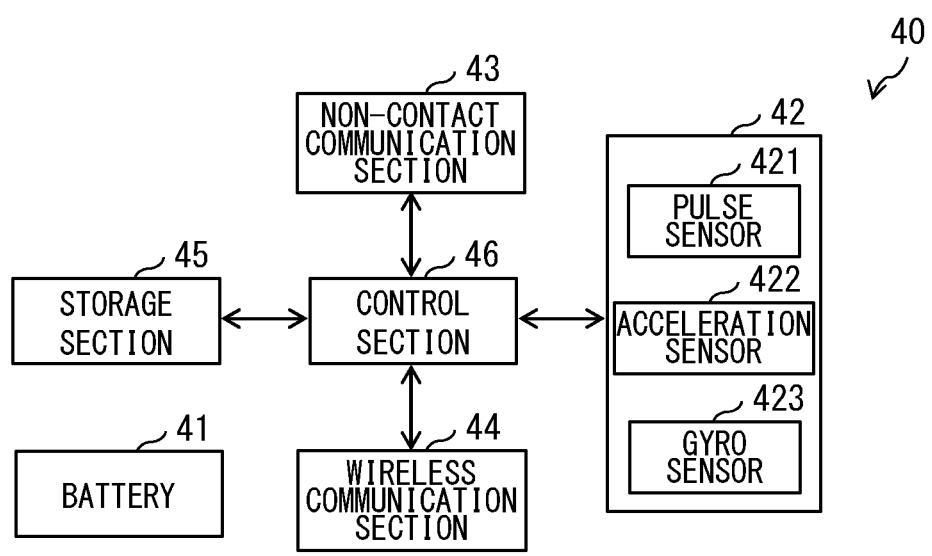

[ FIG. 10 ]
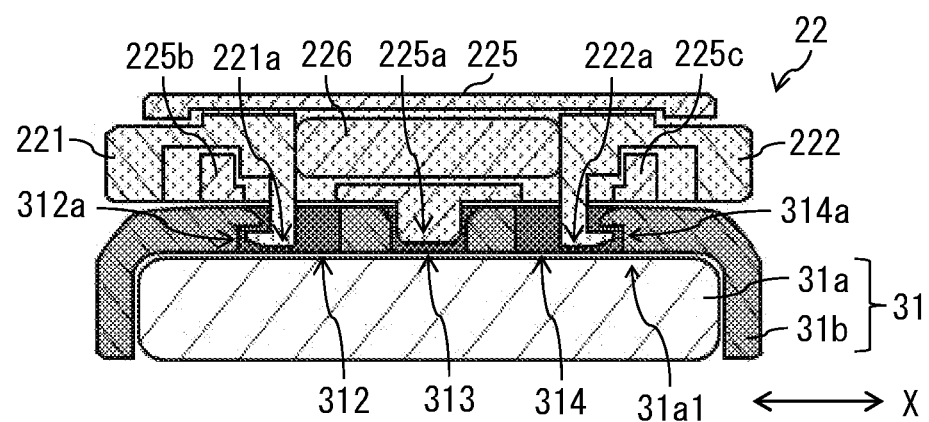
[ FIG. 11 ]
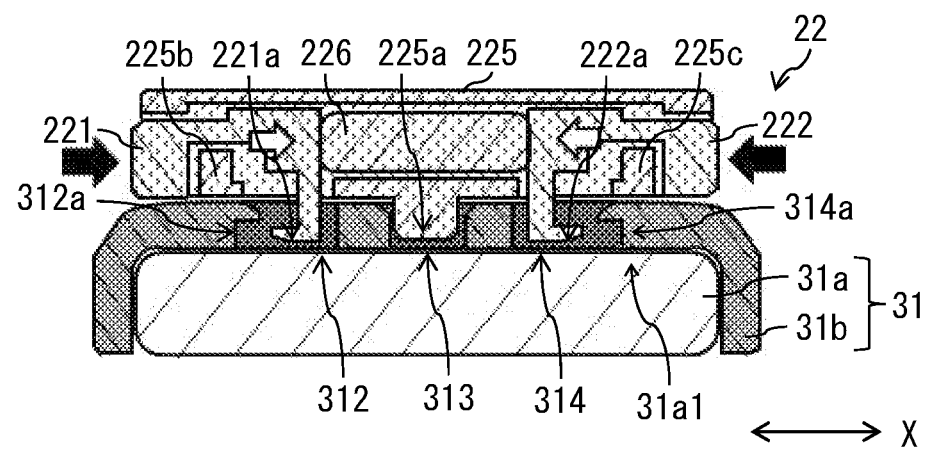

[ FIG. 12 ]
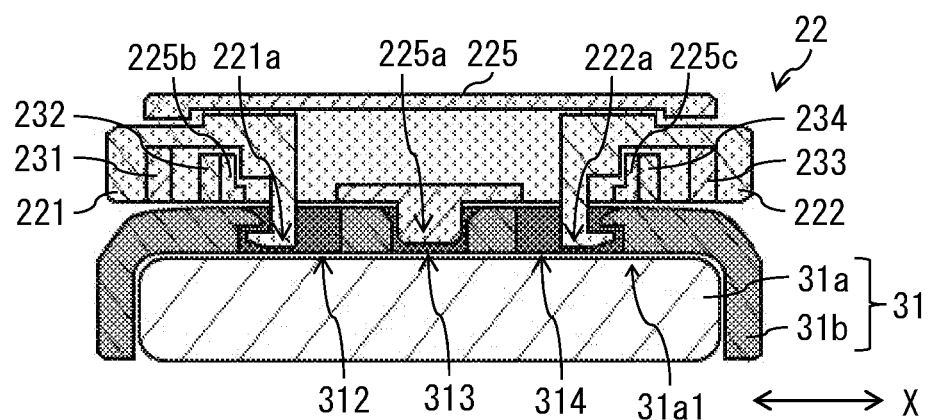
[ FIG. 13 ]
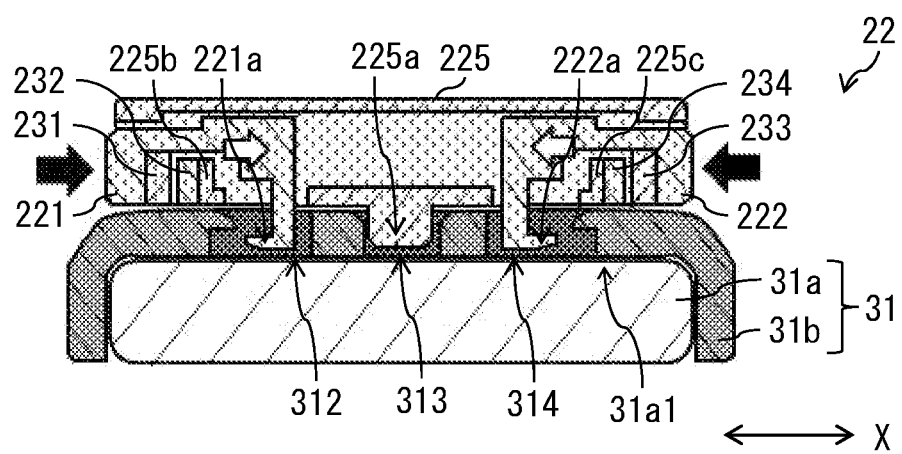

[ FIG. 14 ]
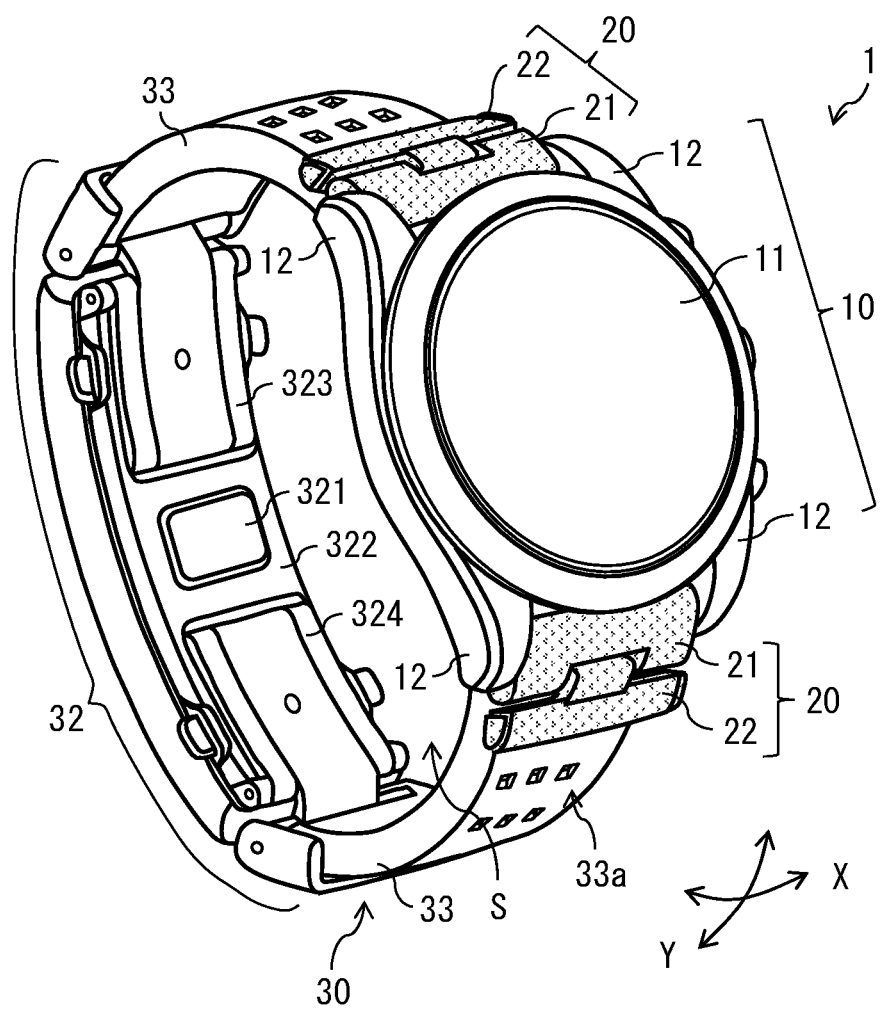

[ FIG. 15 ]
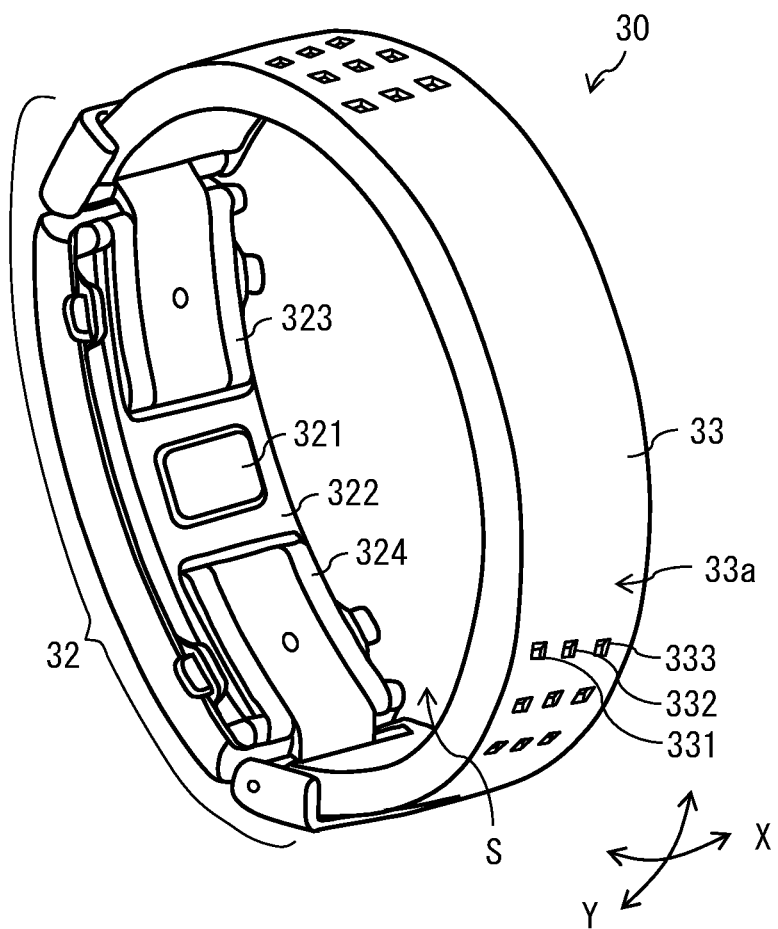

[ FIG. 16 ]
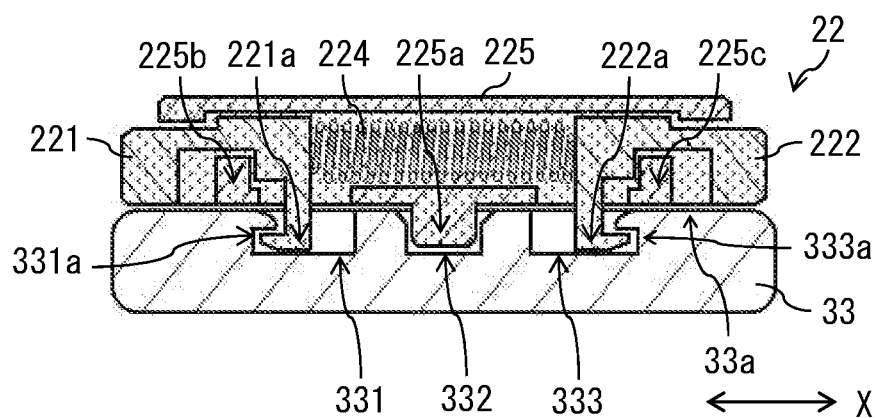
[ FIG. 17 ]
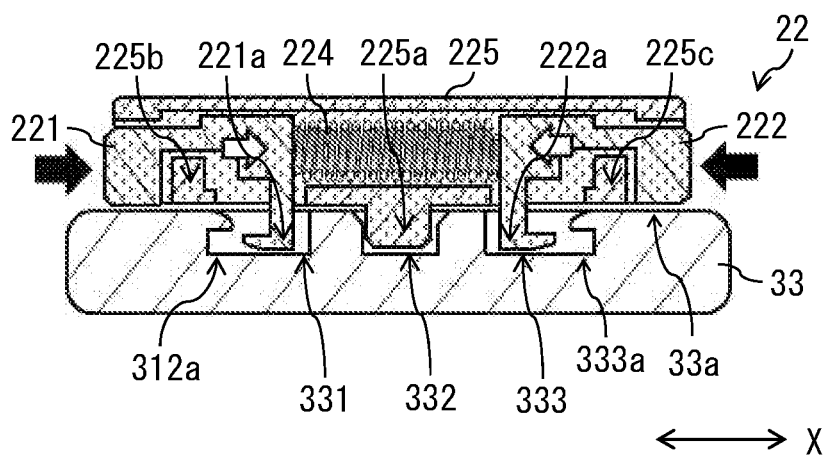

[ FIG. 18 ]
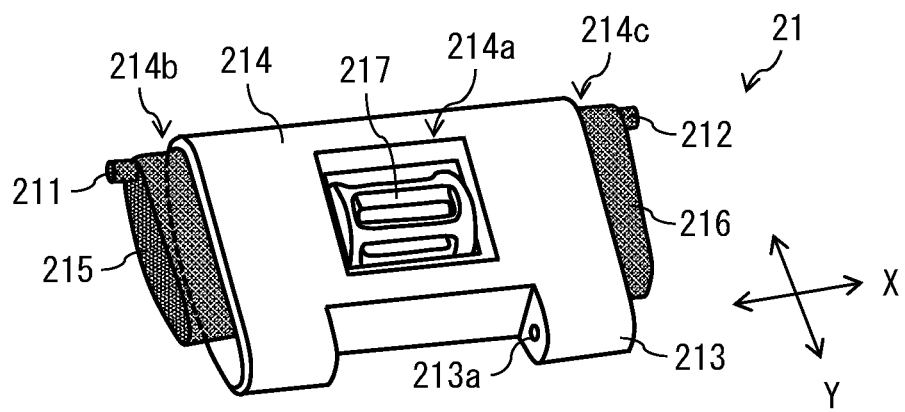
[ FIG. 19 ]
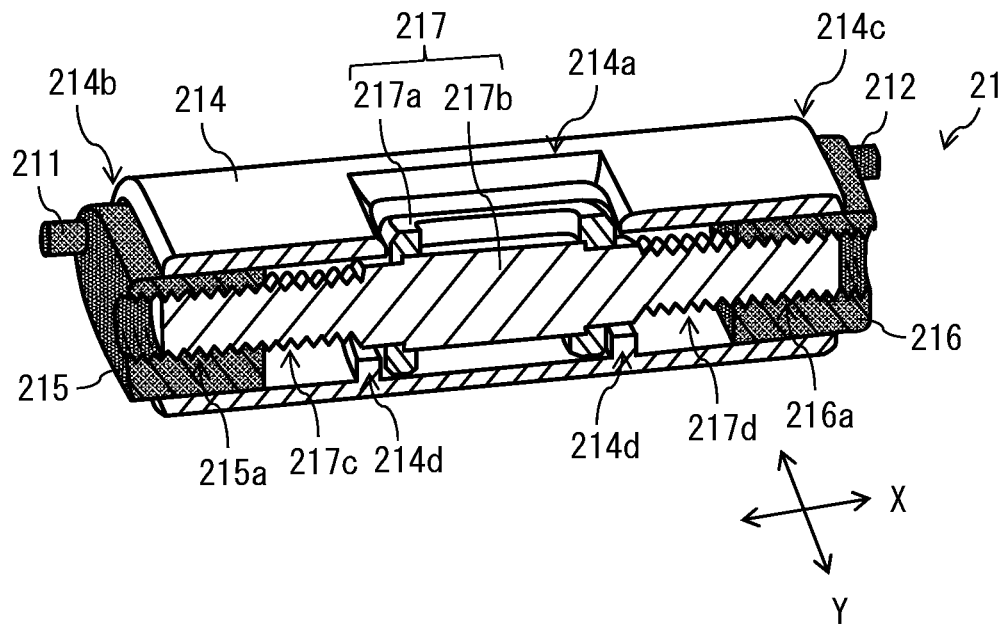

[ FIG. 20 ]
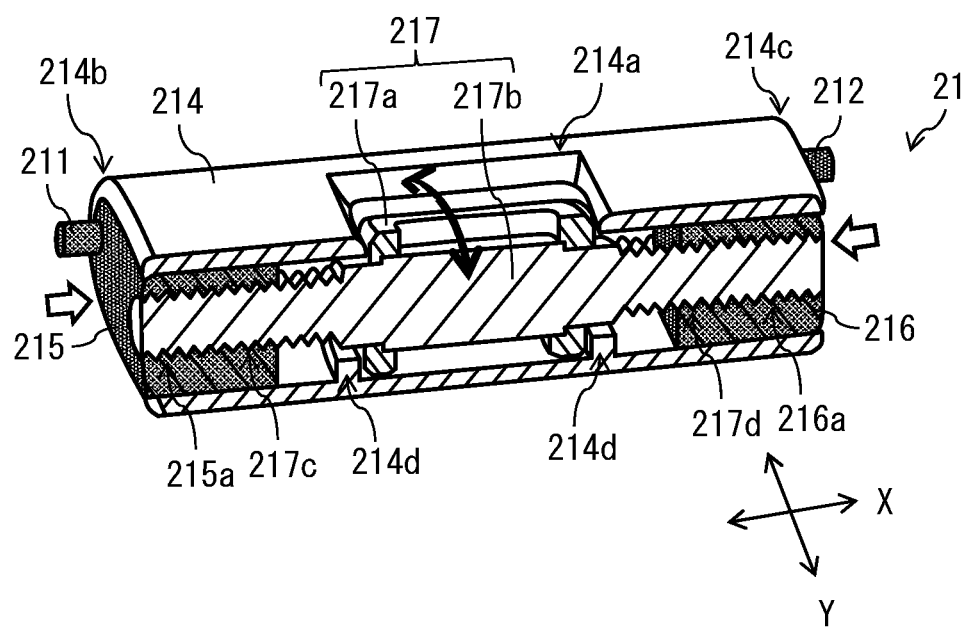

[ FIG. 21 ]
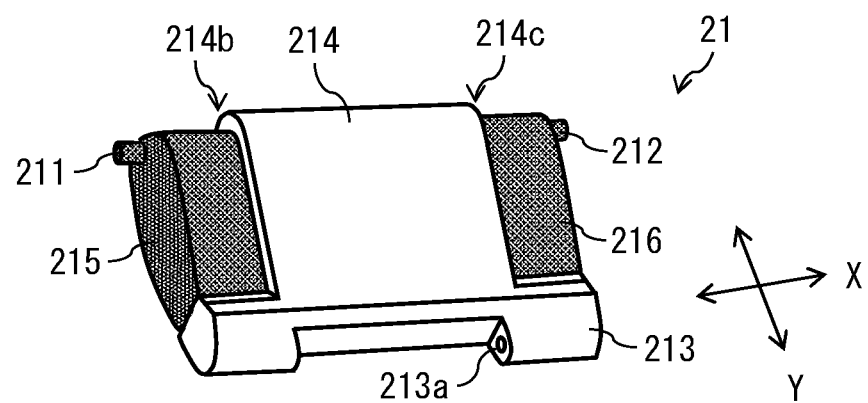
[ FIG. 22 ]
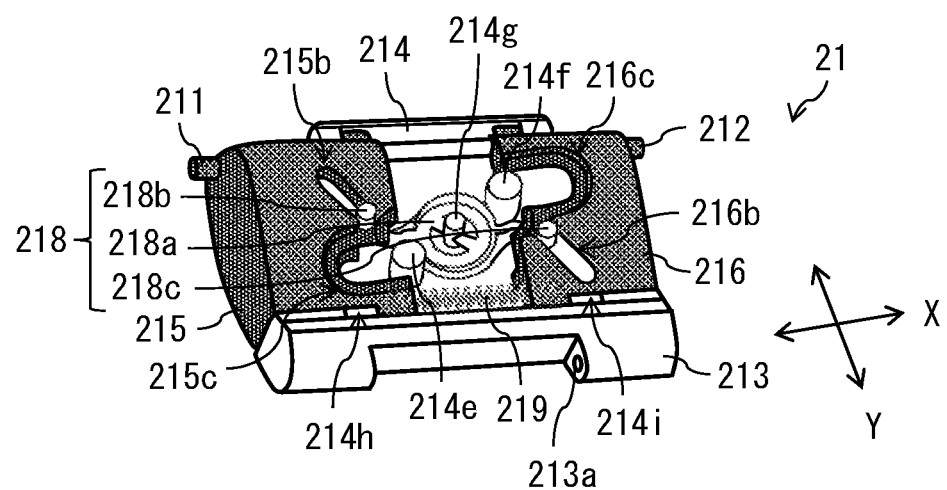

[ FIG. 23 ]
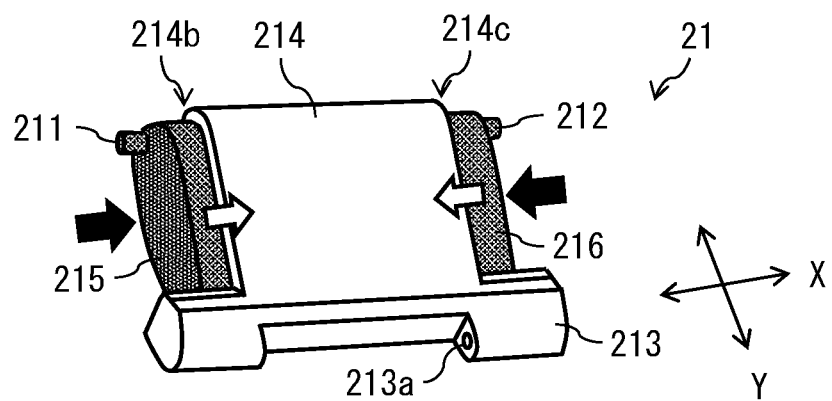
[ FIG. 24 ]
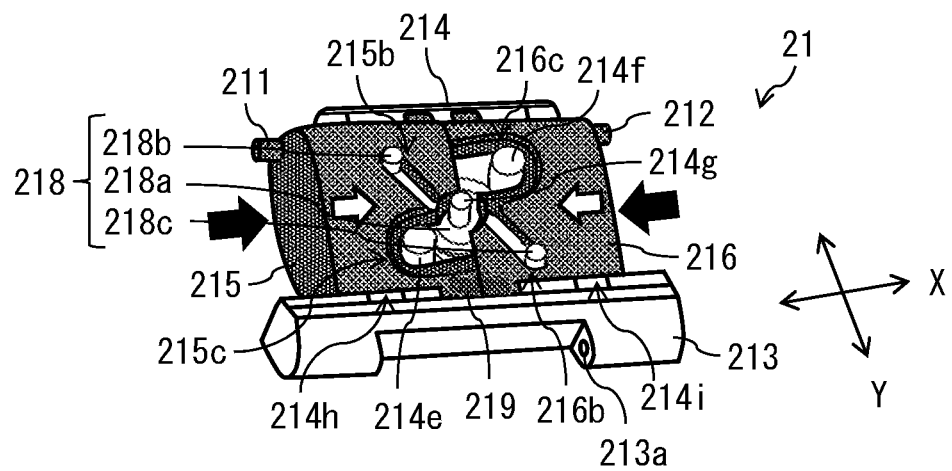

[ FIG. 25 ]
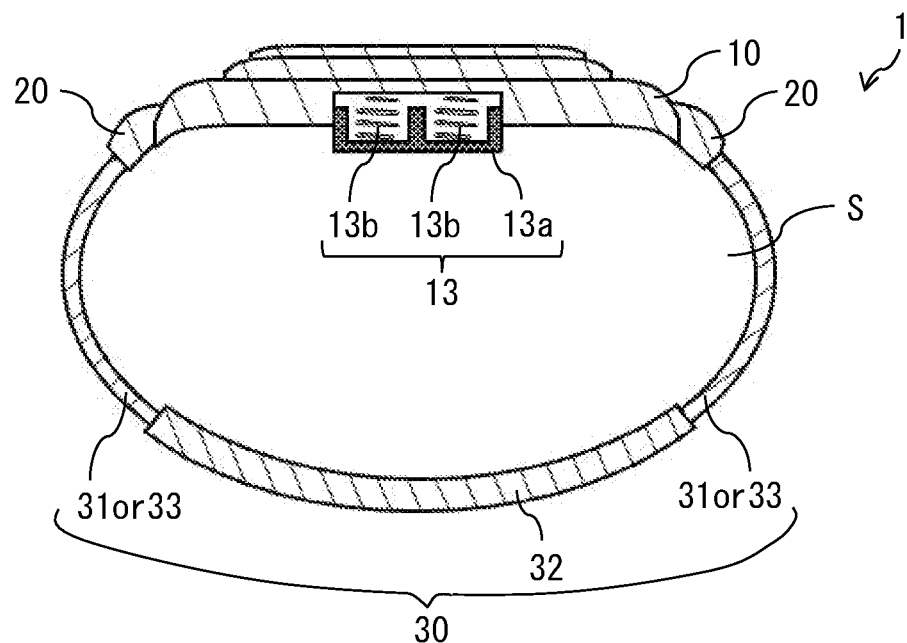
[ FIG. 26 ]
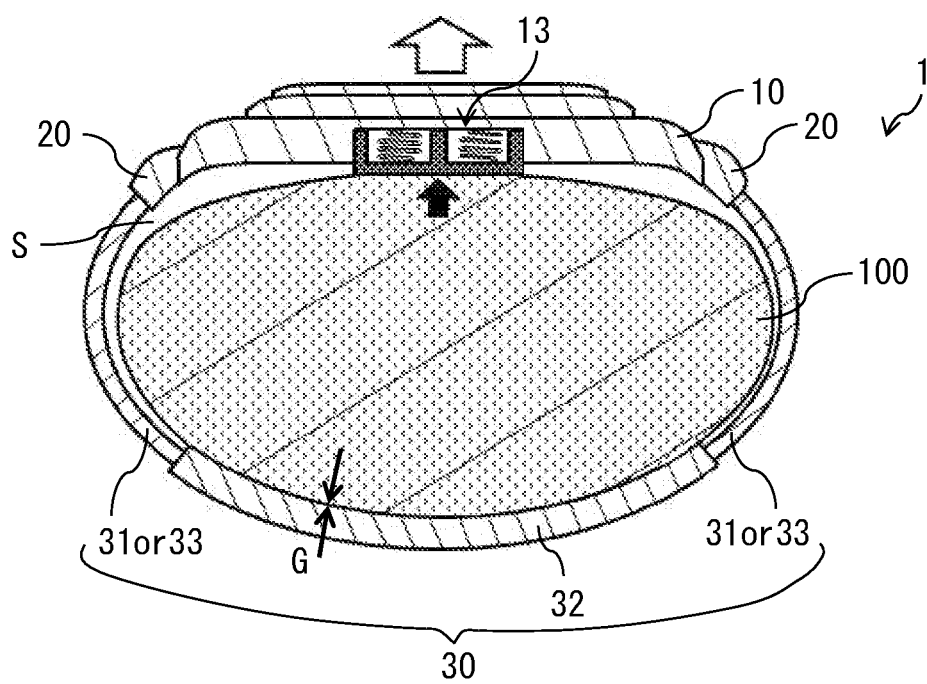

[ FIG. 27 ]
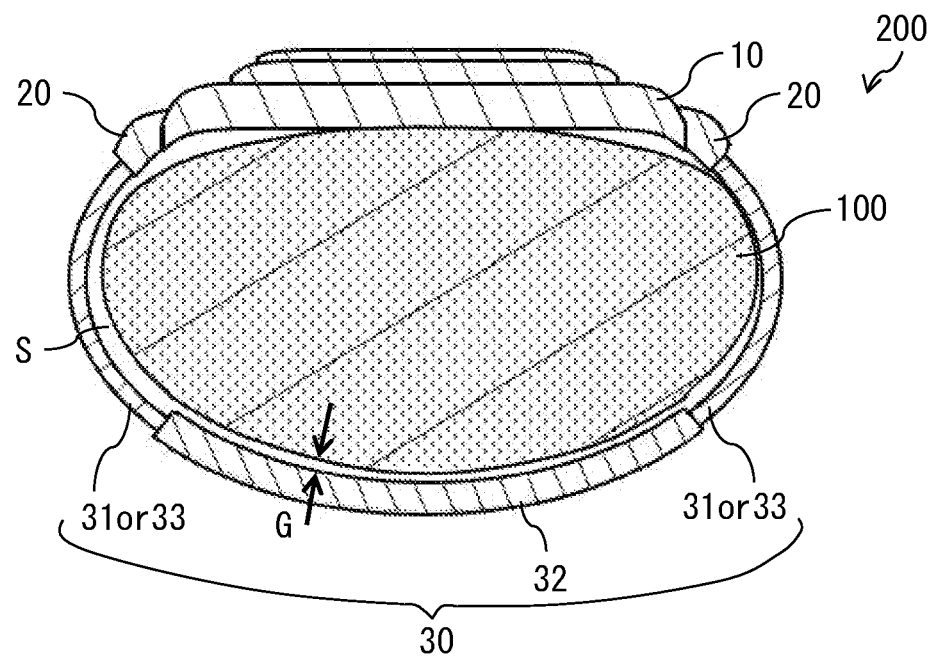

[ FIG. 28 ]
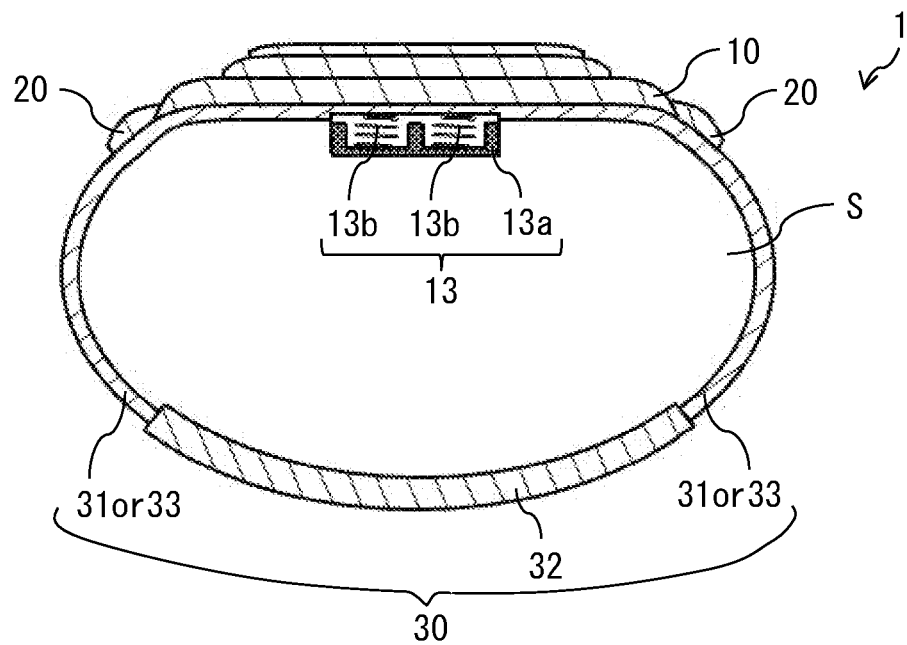
[ FIG. 29 ]
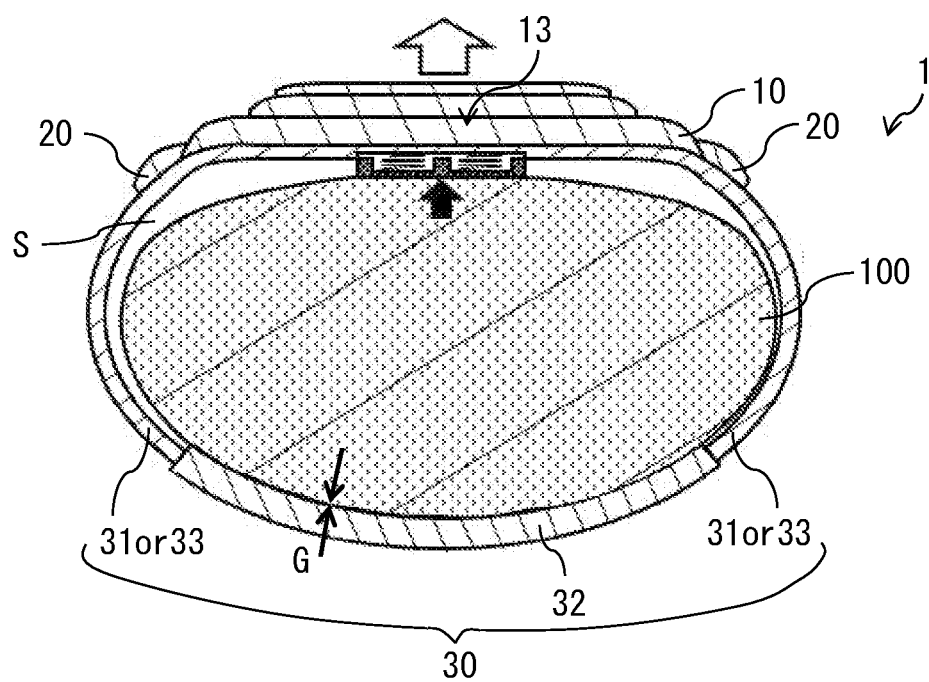

[ FIG. 30 ]
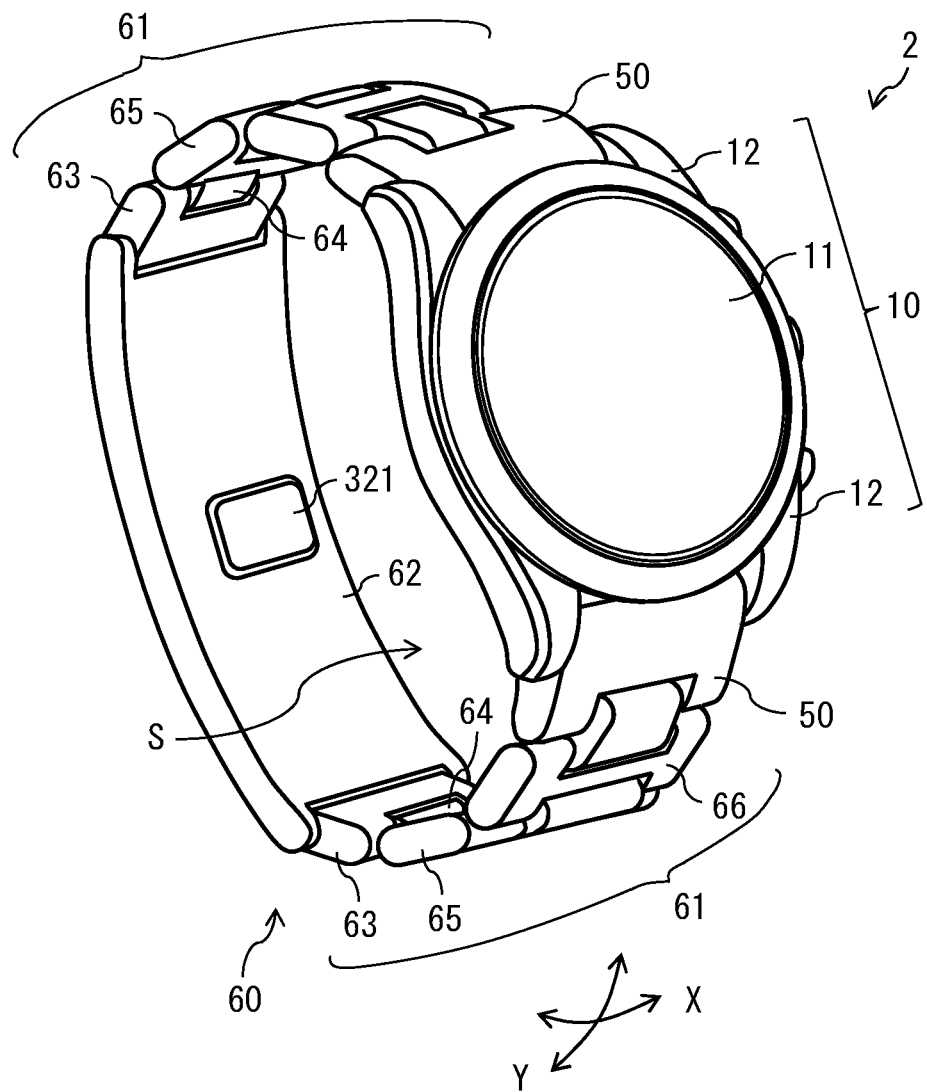

[ FIG. 31 ]
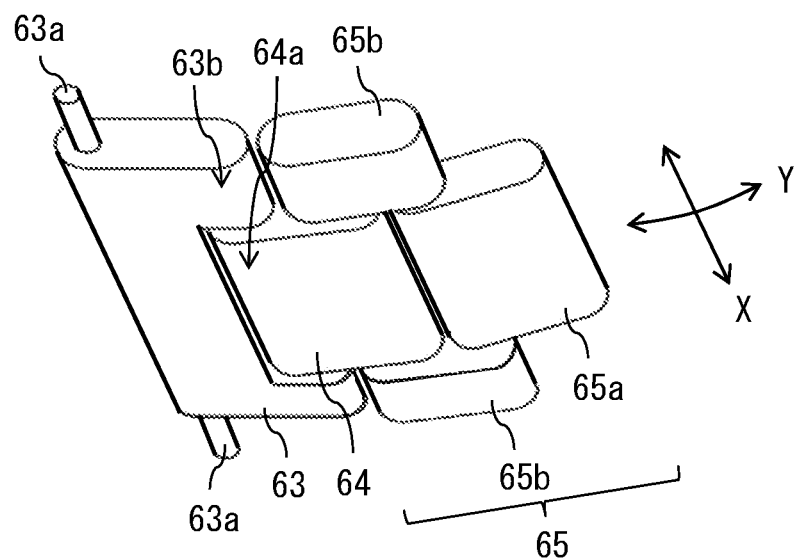
[ FIG. 32 ]
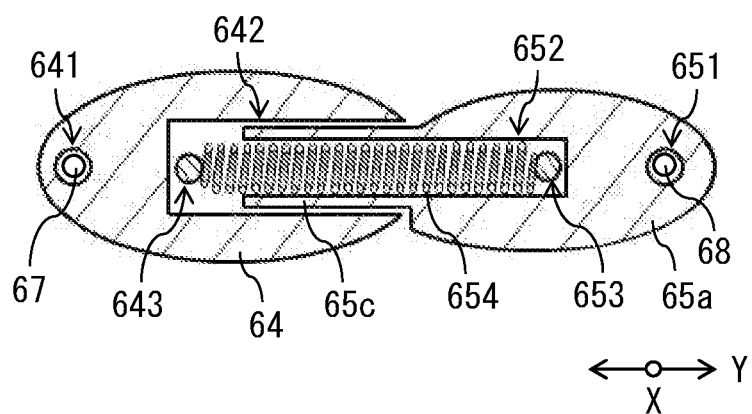

[ FIG. 33 ]
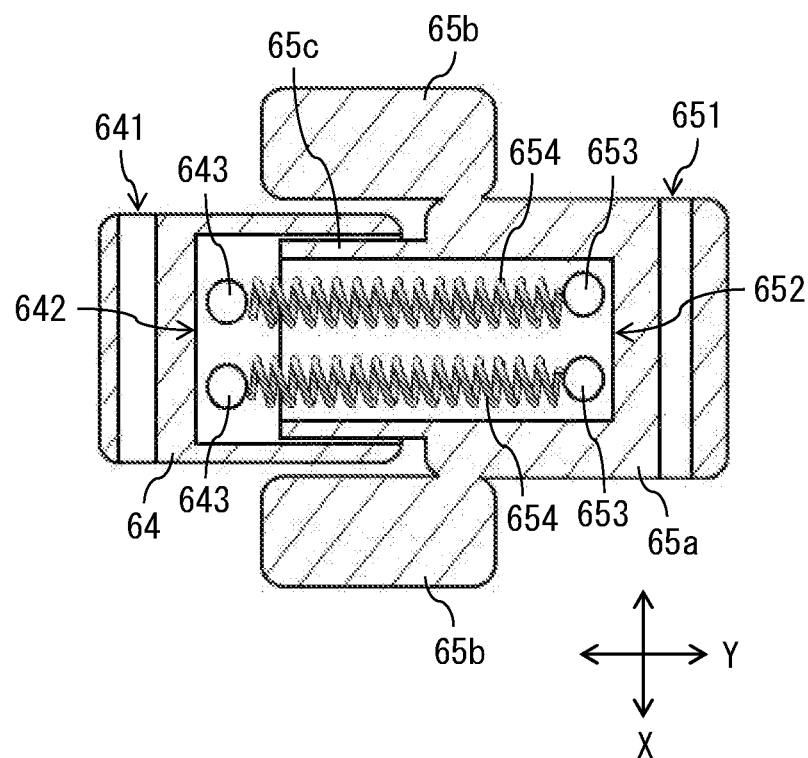
[ FIG. 34 ]
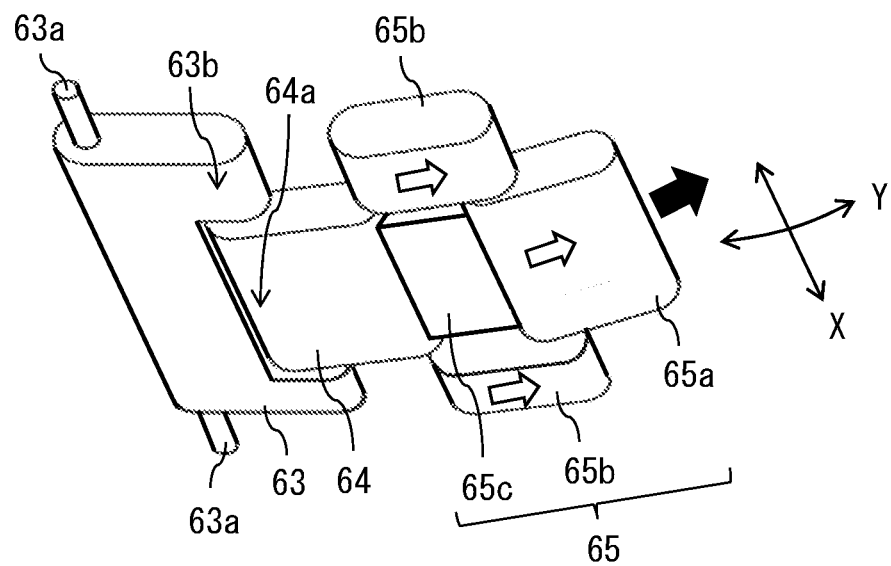

[ FIG. 35 ]
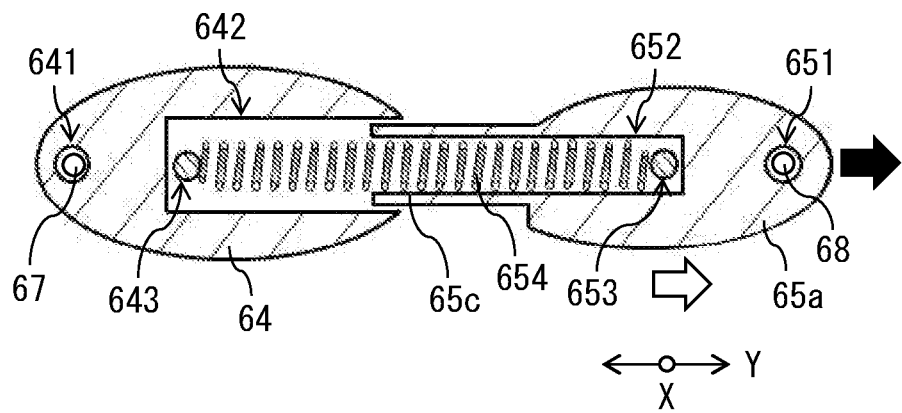
[ FIG. 36 ]
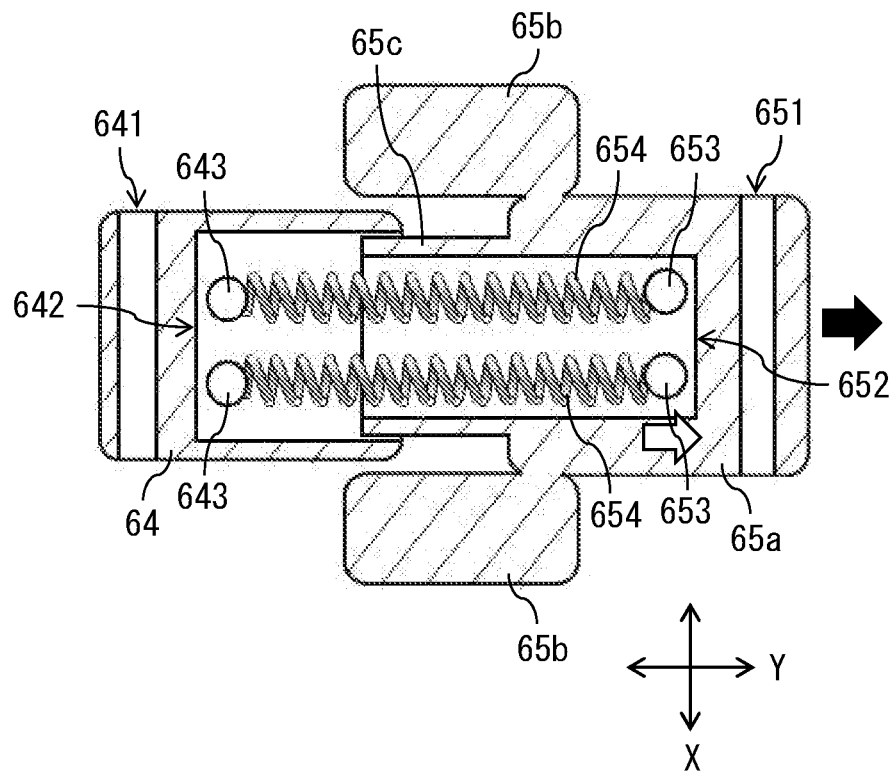

[FIG. 37]
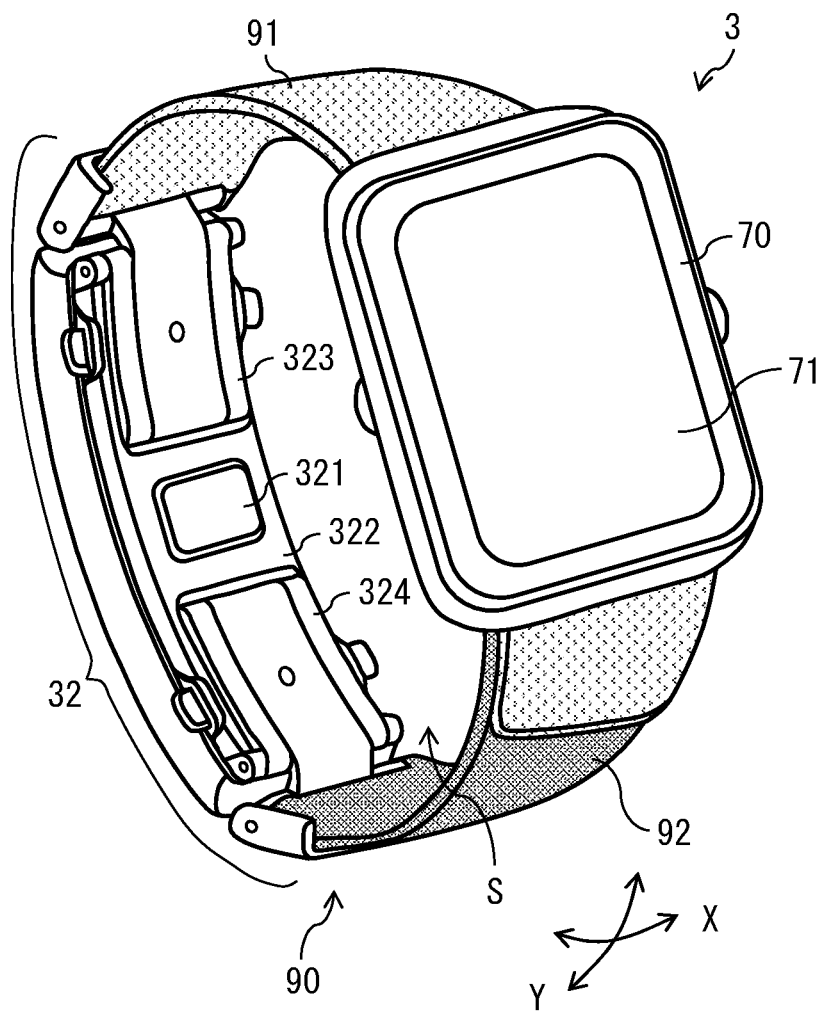

[ FIG. 38 ]
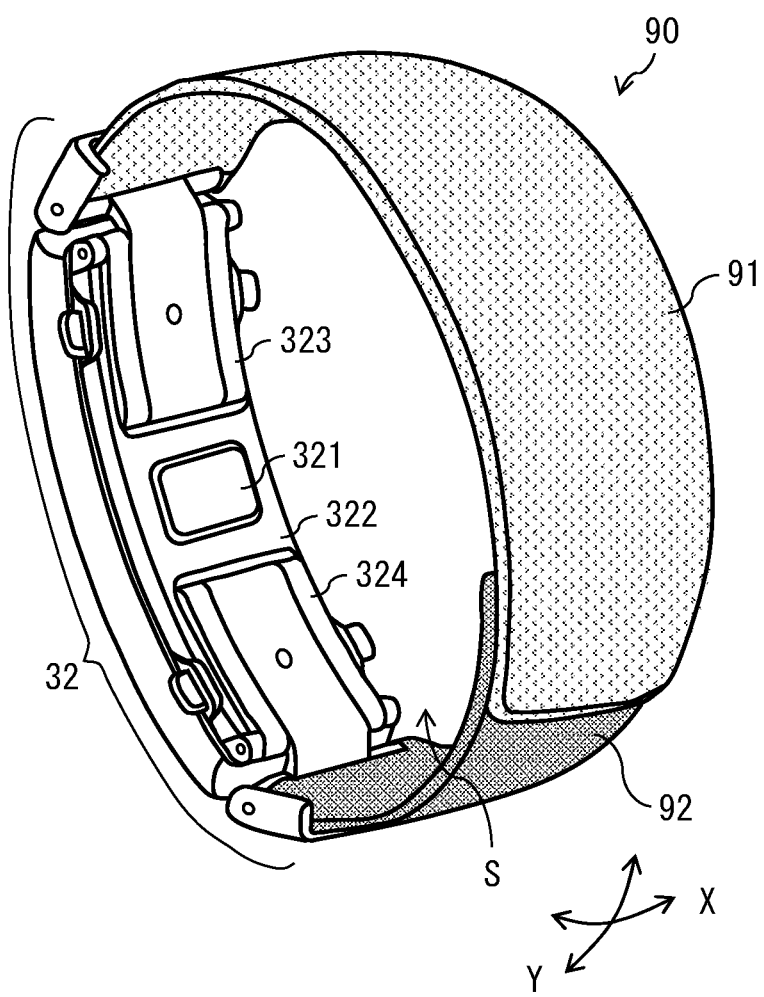

[ FIG. 39 ]
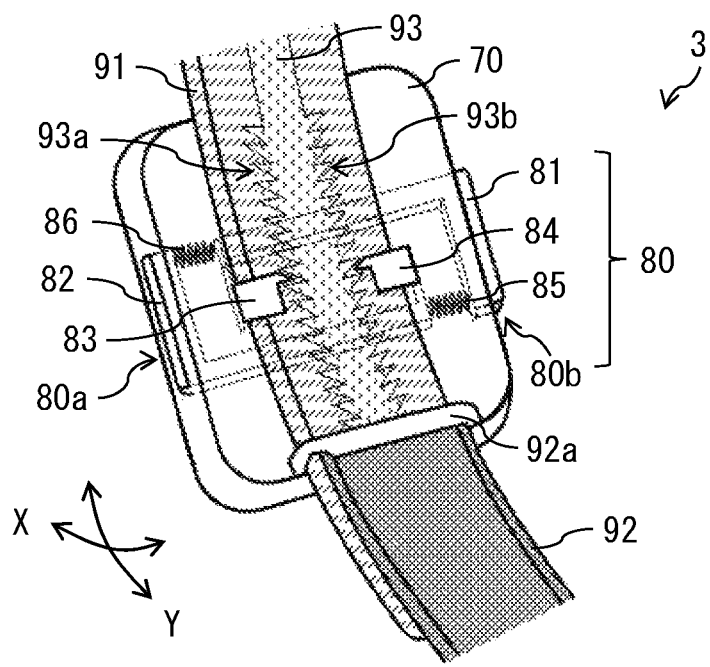
[ FIG. 40 ]
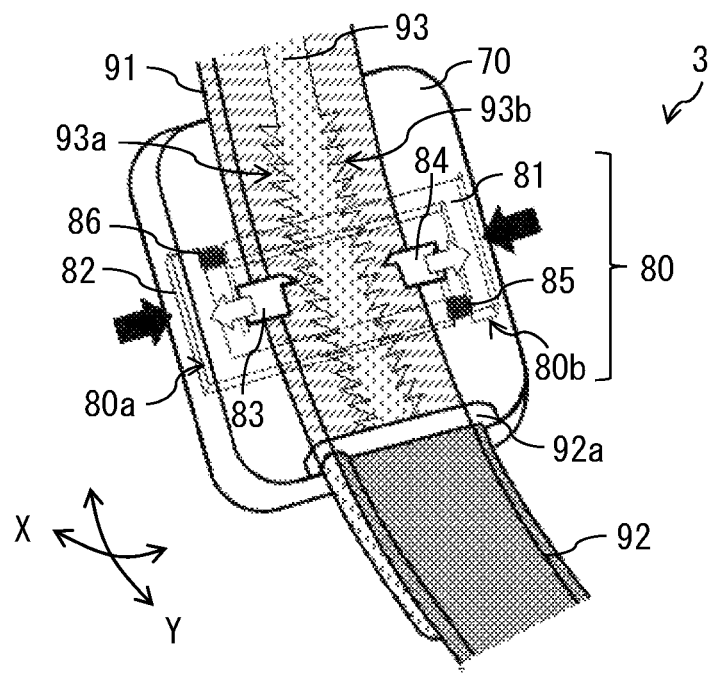

BAND DEVICE, WRISTWATCH, AND END PIECE

CROSS REFERENCE TO RELATED APPLICATIONS

This application is a U.S. National Phase of International Patent Application No. PCT/JP2021/001222 filed on Jan. 15, 2021, which claims priority benefit of Japanese Patent Application No. JP 2020-013153 filed in the Japan Patent Office on Jan. 30, 2020. Each of the above-referenced applications is hereby incorporated herein by reference in its entirety.

TECHNICAL FIELD

The present disclosure relates to a band device, a wristwatch, and an end piece.

BACKGROUND ART

A wristwatch includes a watch head, a band to be wrapped around a wrist, and an end piece that links the watch head and the band together. There is known a structure in which the watch head and the end piece are attached and detached without the use of a tool; this structure enables the watch head of the wristwatch to be easily replaced with another watch head.

In recent years, wearable terminals equipped with information processing functions have been increasingly popular. PTL 1 discloses an electronic apparatus including a circuit substrate in a band, with a watch head and an end piece being detachable and the end piece and the band being detachable. In this electronic apparatus, it is possible to easily replace the watch head and the end piece with another watch head and another end piece for the band.

CITATION LIST

Patent Literature

PTL 1: International Publication No. WO2019/097779

SUMMARY OF THE INVENTION

Incidentally, it has been desired that a variety of watch heads be mounted on an electronic apparatus as described above. It is therefore desirable to provide a band device, a wristwatch, and an end piece that enable a variety of watch heads to be mounted thereon.

A band device according to an aspect of the present disclosure includes a sensor unit, and a band unit that is linked to the sensor unit and forms a hollow part together with the sensor unit. The band unit includes an end piece section to which a watch head section is attached, and an engaging section that makes detachable engagement in a state where the band unit is wrapped around a wrist.

A wristwatch according to an aspect of the present disclosure includes: a sensor unit; a band unit that is linked to the sensor unit and forms a hollow part together with the sensor unit; an end piece section that is detachably linked to the band unit; and a watch head section that is detachably linked to the end piece section. The band unit includes the end piece section to which the watch head section is attached, and an engaging section that makes detachable engagement in a state where the band unit is wrapped around a wrist.

In the band device and the wristwatch according to the respective aspects of the present disclosure, the band unit includes the end piece section to which the watch head section is attached, and the engaging section that makes detachable engagement in a state where the band unit is wrapped around the wrist. Thus, for example, by replacing with the end piece section corresponding to a lug width of a watch head to be replaced in a state where the band unit is wrapped around the wrist, it is possible to replace with a watch head having a different lug width.

An end piece according to an aspect of the present disclosure includes: a linking section that is detachably linked to a watch head section; and an engaging section that detachably engages with a band unit in a state where the band unit is wrapped around a wrist.

In the end piece according to the aspect of the present disclosure, the engaging section is provided that detachably engages with the band unit in a state where the band unit is wrapped around the wrist. Thus, for example, by replacing with the end piece section corresponding to a lug width of a watch head to be replaced in a state where the band unit is wrapped around the wrist, it is possible to replace with a watch head having a different lug width.

BRIEF DESCRIPTION OF THE DRAWINGS

FIG. 1 illustrates a perspective configuration example of a wristwatch according to a first embodiment of the present disclosure.

FIG. 2 is an enlarged view of an end piece unit and a vicinity thereof of the wristwatch in FIG. 1.

FIG. 3 illustrates a perspective configuration example of a band device at the time when a watch head unit and the end piece unit are removed from the wristwatch in FIG. 1.

FIG. 4 is a cross-sectional configuration example of the wristwatch in FIG. 1 as taken along the end piece unit.

FIG. 5 illustrates a state of displacement of the end piece unit in FIG. 4 at the time when the end piece unit in FIG. 4 is pressed from both sides.

FIG. 6 illustrates a perspective configuration example of an engaging part provided in a band section in FIG. 2.

FIG. 7 illustrates a state of displacement of the engaging part at the time when a button of the engaging part provided in the band section in FIG. 2 is pressed.

FIG. 8 is a perspective configuration example of a buckle section in FIG. 1.

FIG. 9 illustrates a functional block example of a circuit substrate provided inside the buckle section in FIG. 1.

FIG. 10 illustrates a modification example of the cross-sectional configuration in FIG. 4.

FIG. 11 illustrates a state of displacement of an end piece unit in FIG. 10 at the time when the end piece unit is pressed from both sides.

FIG. 12 illustrates a modification example of the cross-sectional configuration in FIG. 4.

FIG. 13 illustrates a state of displacement of an end piece unit in FIG. 12 at the time when the end piece unit is pressed from both sides.

FIG. 14 illustrates a modification example of the perspective configuration of the wristwatch in FIG. 1.

FIG. 15 illustrates a perspective configuration example of the band device at the time when the watch head unit and the end piece unit are removed from the wristwatch in FIG. 14.

FIG. 16 illustrates a cross-sectional configuration example as the wristwatch in FIG. 14 is taken along the end piece unit.

FIG. 17 illustrates a state of displacement of the end piece unit in FIG. 16 at the time when the end piece unit is pressed from both sides.

FIG. 18 illustrates a perspective configuration example of a linking section linked to the watch head, provided in the end piece unit in FIG. 1.

FIG. 19 illustrates a cross-sectional configuration example of the linking section in FIG. 18.

FIG. 20 illustrates a state of displacement of the linking section at the time when a rotary portion of the linking section in FIG. 19 is rotated.

FIG. 21 illustrates a perspective configuration example of the linking section to be linked to the watch head, provided in the end piece unit in FIG. 1.

FIG. 22 illustrates an inner configuration example of the linking section in FIG. 21.

FIG. 23 illustrates a state of displacement of the linking section in FIG. 21 at the time when the linking section is pressed from both sides.

FIG. 24 illustrates a state of displacement of the linking section in FIG. 22 at the time when the linking section is pressed from both sides, in which a buckle section 32 is a center blade 322, for example.

FIG. 25 illustrates a modification example of the cross-sectional configuration of the wristwatch in FIG. 1.

FIG. 26 illustrates a state of the wristwatch in FIG. 25 at the time when the wristwatch is worn around a wrist.

FIG. 27 illustrates a state of a wristwatch according to a comparative example at the time when the wristwatch is worn around the wrist.

FIG. 28 illustrates a modification example of the cross-sectional configuration of the wristwatch in FIG. 1.

FIG. 29 illustrates a state of the wristwatch in FIG. 28 at the time when the wristwatch is worn around the wrist.

FIG. 30 illustrates a perspective configuration example of a wristwatch according to a second embodiment of the present disclosure.

FIG. 31 illustrates a perspective configuration example of a portion of a band section in FIG. 30.

FIG. 32 illustrates a cross-sectional configuration example of a portion of the band section in FIG. 31.

FIG. 33 illustrates a cross-sectional configuration example of a portion of the band section in FIG. 31.

FIG. 34 illustrates a state of the band section in FIG. 30 at the time when a portion of the band section is extended.

FIG. 35 illustrates a cross-sectional configuration example of a portion of the band section in FIG. 34.

FIG. 36 illustrates a cross-sectional configuration example of a portion of the band section in FIG. 34.

FIG. 37 illustrates a perspective configuration example of a wristwatch according to a third embodiment of the present disclosure.

FIG. 38 illustrates a perspective configuration example of the band device at the time when the watch head unit and the end piece unit are removed from the wristwatch in FIG. 37.

FIG. 39 illustrates a perspective configuration example of a back surface of the wristwatch in FIG. 37.

FIG. 40 illustrates a state of displacement of an end piece unit in FIG. 39 at the time when the end piece unit is pressed from both sides.

MODES FOR CARRYING OUT THE INVENTION

<1. First Embodiment>

Hereinafter, description is given in detail of modes for carrying out the present disclosure with reference to the drawings. The following description is given of specific examples of the present disclosure, and the present disclosure is not limited to the following embodiments.

FIG. 1 illustrates a perspective configuration example of a wristwatch 1 according to a first embodiment of the present disclosure. The wristwatch 1 includes a watch head unit 10, two end piece units 20, and a band device 30.

(Watch Head Unit 10)

The watch head unit 10 includes a display section 11 and four lugs 12. The display section 11 has a display surface that displays time. The display section 11 may include a dial face, an hour hand, and a minute hand on the display surface, and may be configured to display time by the hour hand and the minute hand pointing to any position on the dial face. The display section 11 may be configured by a liquid crystal display, and may be configured to display, on the display surface, a screen to indicate time on the liquid crystal display. The screen may be a screen simulating an analog watch, or may be a screen that digitally displays time. The watch head unit 10 may have functions of a smartwatch.

Each lug 12 is linked to the display section 11. Each lug 12 projects along an extending direction of a band section 31 (hereinafter, referred to as a "Y direction" as appropriate) described later. The Y direction corresponds to a specific example of a "second direction" of the present disclosure. Two lugs 12 of the four lugs 12 extend from the upper side of the display section 11 toward the band section 31 to be provided at positions opposed to each other with the band section 31 interposed therebetween. The remaining two lugs 12 of the four lugs 12 extend from the lower side of the display section 11 toward the band section 31 to be provided at positions opposed to each other with the band section 31 interposed therebetween. The "upper side of the display section 11" refers to the upper side of time displayed on the display section 11, and the "lower side of the display section 11" refers to the lower side of the time displayed on the display section 11. Each lug 12 is detachably linked to the end piece unit 20. Each lug 12 has, for example, a hole 121 as illustrated in FIG. 2. A pin 211 or a pin 212 of the end piece unit 20 is inserted into the hole 121. FIG. 2 illustrates the end piece unit 20 and a vicinity thereof in an enlarged manner.

(End Piece Unit 20)

The two end piece units 20 are provided at positions opposed to each other with the watch head unit 10 interposed therebetween. One end piece unit 20 is disposed in an interval portion between the two lugs 12 provided on the upper side of the watch head unit 10, and is linked to the two lugs 12 provided on the upper side of the watch head unit 10. Another end piece unit 20 is disposed in an interval portion between the two lugs 12 provided on the lower side of the watch head unit 10, and is linked to the two lugs 12 provided on the lower side of the watch head unit 10. The two end piece units 20 are further linked to the band device 30.

As illustrated in FIG. 2, the end piece unit 20 includes, for example, a linking section 21 that is detachably linked to the two lugs 12 opposed to each other with a predetermined lug width therebetween, and an engaging section 22 detachably engaging with the band device 30. The engaging section 22 is detachably linked to the band device 30. The linking section 21 and the engaging section 22 are arranged side by side along the extending direction (Y direction) of the band section 31. A portion (a projecting part 223) of the engaging section 22 is accommodated in a recess 213 of the linking section 21, and a pin penetrating the projecting part 223 is inserted into a hole provided on each side wall of the recess 213. This allows the linking section 21 and the engaging section 22 to be linked to each other rotatably about the pin, as a rotational axis, penetrating the projecting part 223. The engaging section 22 includes movable parts 221 and 222 provided on both sides. Description is given later in detail of configurations and operations of the movable parts 221 and 222.

(Band Device 30)

As illustrated in FIG. 3, the band device 30 has an annular shape, for example, and forms a hollow part S. FIG. 3 illustrates a perspective configuration example of the band device 30 at the time when the watch head unit 10 and the end piece unit 20 are removed from the wristwatch 1. The band device 30 includes, for example, the band section 31 and a buckle section 32. The buckle section 32 corresponds to a specific example of a "sensor unit" of the present disclosure. One end of the band section 31 is linked to one end of the buckle section 32, and another end of the band section 31 is linked to another end of the buckle section 32. A circuit substrate 40 (described later) is mounted on the buckle section 32. The circuit substrate 40 is equipped with a sensor function and a wireless communication function, and a pulse sensor 421 (described later) that serves a portion of the sensor function is exposed on an inner surface of the buckle section 32 (an inner surface of the band device 30). FIG. 1 illustrates a state where a detection electrode 321 of the pulse sensor 421 (described later) is exposed on the inner surface of the buckle section 32 (inner surface of the band device 30).

The band section 31 forms the hollow part S together with the buckle section 32. The band section 31 includes, for example, a flexible base material 31a and an engaging part 31b in contact with an outer surface 31a1, of the base material 31a, on side opposite to side of the hollow part S. The base material 31a is, for example, a flexible sheet base material configured by a resin material such as rubber. Both side surfaces of the base material 31a are provided with multiple through-holes 311 arranged side by side in the extending direction (Y direction) of the band section 31 with a predetermined gap interposed therebetween.

The engaging part 31b is formed on the outer surface 31a1, of the base material 31a, on the side opposite to the side of the hollow part S. The engaging part 31b is configured to be detachable from the base material 31a, and is configured to be detachable from the engaging section 22 of the end piece unit 20. The engaging part 31b has multiple recesses 312, 313, and 314, for example, as illustrated in FIG. 2. The multiple recesses 312, 313, and 314 are arranged in a direction orthogonal to the extending direction (Y direction) of the band section 31 on the outer surface 31a1. On the outer surface 31a1, the direction orthogonal to the extending direction (Y direction) of the band section 31 corresponds to a width direction (hereinafter, referred to as an "X direction" as appropriate) of the band section 31. The outer surface 31a1 of the band section 31 may be exposed to each bottom surface of the multiple recesses 312, 313, and 314. In a case where the outer surface 31a1 of the band section 31 is exposed to each bottom surface of the multiple recesses 312, 313, and 314, the multiple recesses 312, 313, and 314 are each a through-hole for the engaging part 31b. The recesses 312 and 314 each correspond to a specific example of a "recess" or a "first recess" of the present disclosure. The recess 313 corresponds to a specific example of a "shift suppressing section" or a "second recess" of the present disclosure. The X direction corresponds to a specific example of a "second direction" of the present disclosure.

Among the multiple recesses 312, 313, and 314 arranged side by side in the width direction (X direction) of the band section 31, the recesses 312 and 314 positioned at both ends are configured to be detachably engaged with the engaging section 22 of the end piece unit 20 in the width direction (X direction) of the band section 31. The recess 312 is provided to be adjacent to a left end edge of the band section 31 in the width direction (X direction). The recess 314 is provided to be adjacent to a right end edge of the band section 31 in the width direction (X direction). The left end edge of the band section 31 in the width direction (X direction) refers to an end edge of the band section 31, positioned on the left side of time displayed on the display section 11. The right end edge of the band section 31 in the width direction (X direction) refers to an end edge of the band section 31, positioned on the right side of time displayed on the display section 11.

The recess 312 has, for example, a depression 312a projecting toward the left end edge of the band section 31 in the width direction (X direction) as illustrated in FIG. 4. An engaging portion 221a described later engages with this depression 312a. FIG. 4 illustrates a cross-sectional configuration example as the wristwatch 1 is taken along the end piece unit 20. The recess 314 has, for example, a depression 314a projecting toward a right end edge of the band section 31 in the width direction (X direction) as illustrated in FIG. 4. An engaging portion 222a described later engages with this depression 314a. The recess 313 suppresses shifting of the end piece unit 20 at least in the X direction of the X direction and the Y direction at the time when the engaging portions 221a and 222a of the end piece unit 20 engage with the recesses 312 and 314. The recess 313 is provided at a location corresponding to a protrusion 225a fixed to a casing 225 of the end piece unit 20, and accommodates the protrusion 225a. The protrusion 225a described later is inserted into the recess 313. When the protrusion 225a is inserted into the recess 313, the recess 313 surrounds side surfaces of the protrusion 225a from four sides with a predetermined gap interposed therebetween. When the protrusion 225a is inserted into the recess 313, the recess 313 may be in contact with at least two side surfaces, of the side surfaces of the protrusion 225a, opposed to each other in the X direction. This suppresses shifting of the end piece unit 20 at least in the X direction of the X direction and the Y direction.

(Engaging Section 22)

Next, description is given in detail of the engaging section 22. The engaging section 22 includes, for example, the movable parts 221 and 222 provided for respective sides as illustrated in FIG. 4. The movable part 221 is provided to correspond to each of the recesses 312 and 314, and the movable part 222 is provided to correspond to the recess 314. The movable parts 221 and 222 are disposed to be opposed to each other with a predetermined gap interposed therebetween in the width direction (X direction) of the engaging section 22. The left end of the movable part 221 is exposed from an opening provided at a left end edge of the engaging section 22. Further, the engaging portion 221a to engage with the depression provided in the recess 312 is provided at the right end of the movable part 221. The right end of the movable part 222 is exposed from an opening provided at a right end edge of the engaging section 22. Further, the engaging portion 222a to engage with the depression provided in the recess 314 is provided at the left end of the movable part 222. The engaging section 22 includes, for example, an elastic member 224 provided in a gap between the movable part 221 and the movable part 222 as illustrated in FIG. 4. For example, the elastic member 224 is configured by a spring that energizes the movable part 221 toward side of the left end edge of the engaging section 22, and energizes the movable part 222 toward side of the right end edge of the engaging section 22.

The engaging section 22 includes, for example, the casing 225 that accommodates the movable parts 221 and 222 and the elastic member 224 as illustrated in FIG. 4. The casing 225 is provided with multiple openings. The casing 225 is provided with, for example, an opening that exposes the left end of the movable part 221, an opening that exposes the right end of the movable part 222, an opening that exposes the engaging portion 221a, and an opening that exposes the engaging portion 222a.

The casing 225 includes, for example, the protrusion 225a and ribs 225b and 225c fixed to the casing 225, as illustrated in FIG. 4. The protrusion 225a protrudes from a back surface of the casing 225 (a surface on side of the band section 31) to side of the recess 313 of the band section 31. The insertion of the protrusion 225a into the recess 313 suppresses shifting of the end piece unit 20 at least in the X direction. The ribs 225b and 225c are standing walls that project into a gap inside the casing 225. The rib 225b prevents the movable part 221 energized by the elastic member 224 toward the side of the left end edge of the engaging section 22 from falling from the engaging section 22. The rib 225c prevents the movable part 222 energized by the elastic member 224 toward the side of the right end edge of the engaging section 22 from falling from the engaging section 22.

FIG. 5 illustrates a state of displacement of the end piece unit 20 at the time when the movable parts 221 and 222 are pressed from both sides. As illustrated in FIG. 5, pressing the movable parts 221 and 222 from the both sides causes the engaging portion 221a of the movable part 221 to be disengaged from the depression 312a of the recess 312 and causes the engaging portion 222a of the movable part 222 to be disengaged from the depression 314a of the recess 314. This enables the end piece unit 20 to be disengaged from the band section 31 in a state where the band section 31 is wrapped around a wrist. Meanwhile, canceling the pressing on the movable parts 221 and 222 allows the engaging portion 221a of the movable part 221 to engage with the depression 312a of the recess 312, and allows the engaging portion 222a of the movable part 222 to engage with the depression 314a of the recess 314, as illustrated in FIG. 4. This enables the end piece unit 20 to be fixed to the band section 31 in a state where the band section 31 is wrapped around the wrist. That is, the engaging section 22 is configured to make detachable engagement in a state where the band section 31 is wrapped around the wrist. In other words, the engaging part 31b is configured to make detachable engagement in a state where the end piece unit 20 and the band section 31 are wrapped around the wrist.

(Engaging Part 31b)

Next, description is given of another aspect of the engaging part 31b provided in the band section 31. FIG. 6 illustrates a perspective configuration example of the engaging part 31b. FIG. 7 illustrates a state of displacement of the engaging part 31b at the time when a button portion 318 of the engaging part 31b is pressed. The engaging part 31b is configured to be detachable from the base material 31a. The engaging part 31b includes, for example, a first member 315 in contact with the outer surface 31a1 of the base material 31a, a second member 316 in contact with a left side surface of the base material 31a, and a rotational axis 317 linking the left end of the first member 315 and the second member 316 together. Although not illustrated in FIGS. 6 and 7, the first member 315 is provided with the multiple recesses 312, 313, and 314. The second member 316 includes a pin 315a to be inserted into a through-hole 311 of the base material 31a.

The engaging part 31b further includes, for example, the button portion 318 inserted into the right end of the first member 315. The button portion 318 includes an elastic member 318c that energizes, when the button portion 318 is pressed in the Y direction, the button portion 318 in a direction opposite to the pressing direction, a support 318b that supports the elastic member 318c, and a support 318a that supports the pin 315a. The elastic member 318c is configured by a spring or the like, for example. In a case where the elastic member 318c is configured by a spring, the support 318b is configured by a rod-shaped member penetrating the spring. When the button portion 318 is pressed in the Y direction, the support 318a is configured to be able to cancel the support for the pin 315a and to detach the pin 315a from the support 318a. In a case where the support for the pin 315a by the support 318a is canceled in a state where the pin 315a is inserted into the through-hole 311 of the base material 31a, for example, the first member 315 is rotated about the rotational axis 317 as a central axis, and the pin 315a is pulled out of the through-hole 311 of the base material 31a to thereby cause the engaging part 31b to be detached from the base material 31a, as illustrated in FIG. 7.

(Buckle Section 32)

Next, description is given in detail of the buckle section 32. FIG. 8 illustrates a perspective configuration example of the buckle section 32. FIG. 8 illustrates an open state of the buckle section 32. A closed state of the buckle section 32 is illustrated in FIG. 1. The buckle section 32 includes, for example, a center blade 322, a movable blade 323, and a movable blade 324.

The movable blade 323 includes links 323a and 323b. One end of the link 323a is coupled to one end of the center blade 322 via a joint 325a, and another end of the link 323a is coupled to one end of the link 323b via a joint 326a. One end of the band section 31 is coupled to another end of the link 323b. The movable blade 324 includes links 324a and 324b. One end of the link 324a is coupled to another end of the center blade 322 via a joint 325b, and another end of the link 324a is coupled to one end of the link 324b via a joint 326b. The other end of the band section 31 is coupled to another end of the link 324b.

In the closed state of the buckle section 32, the links 323a and 323b of the movable blade 323 are folded on side of the one end of the center blade 322, and the links 324a and 324b of the movable blade 324 are folded on side of the other end of the center blade 322. The movable blades 323 and 324 are provided to have an interval therebetween in this closed state. Thus, as illustrated in FIG. 8, it is possible to expose the detection electrode 321 of the pulse sensor 421 to the interval portion between the movable blade 323 and the movable blade 324.

The buckle section 32 transitions from the closed state to the open state by canceling the folding of the movable blades 323 and 324. Specifically, the link 323a of the movable blade 323 rotates about the joint 325a and the link 323b rotates about the joint 326a, and the link 324a of the movable blade 324 rotates about the joint 325b and the link 324b rotates about the joint 326b, thereby canceling the folding of the movable blades 323 and 324. In the open state of the buckle section 32, the length of the outer circumference of the band device 30 is increased, thus enabling a wearer to pass the band device 30 through the arm and to remove the band device 30 from the arm.

(Circuit Substrate 40)

The center blade 322 incorporates the circuit substrate 40. The circuit substrate 40 includes, for example, a battery 41, a sensor module 42, a non-contact communication section 43, a wireless communication section 44, a storage section 45, and a control section 46, as illustrated in FIG. 9.

The battery 41 is a secondary cell that supplies power to each component of the circuit substrate 40. The sensor module 42 is a module that detects one or two or more physical quantities. In the example illustrated in FIG. 9, the pulse sensor 421, an acceleration sensor 422, and a gyro sensor 423 are exemplified as sensors included in the sensor module 42. A sensor included in the sensor module 42 is not limited to the example illustrated in FIG. 9; the sensor module 42 may include another sensor or may not include some or all of the sensors illustrated in FIG. 9.

The non-contact communication section 43 is an interface to perform non-contact communication with another communication apparatus. Examples of use cases of the non-contact communication between the non-contact communication section 43 and the other communication apparatus include payment of goods at a retail store, payment of a fare at a station gate, and identification.

The wireless communication section 44 is an interface to perform wireless communication with another communication apparatus over a wider communicable range than the non-contact communication. The wireless communication section 44 may perform wireless communication using a wireless LAN, or may perform wireless communication using Bluetooth (registered trademark). The wireless communication section 44 is used, for example, upon transmission of information detected by the sensor module 42 to a smartphone used by the wearer.

The storage section 45 stores information to be used for an operation of the circuit substrate 40. For example, the storage section 45 stores a program for the control section 46 to operate and information detected by the sensor module 42. The control section 46 controls overall operations of the circuit substrate 40. The control section 46 controls, for example, starting and stopping of the sensor module 42, the non-contact communication performed by the non-contact communication section 43, and the wireless communication performed by the wireless communication section 44.

Effects

Next, description is given of effects of the wristwatch 1 according to the present embodiment.

In the present embodiment, the engaging section 22 of the end piece unit 20 is configured to make detachable engagement in a state where the band section 31 is wrapped around the wrist. Thus, for example, by replacing with the end piece unit 20 corresponding to the lug width of the watch head unit 10 to be replaced in a state where the band section 31 is wrapped around the wrist, it is possible to replace with the watch head unit 10 having a different lug width. Thus, it is possible to mount a variety of the watch head units 10.

In the present embodiment, the engaging section 22 is formed on the outer surface 31a1, of the band section 31, on the side opposite to the side of the hollow part S. This makes it possible to attach and detach the end piece unit 20 and the band section 31 via the engaging section 22, for example, in a state where the band section 31 is wrapped around the wrist. Thus, it is possible to mount a variety of the watch head units 10.

In the present embodiment, the multiple recesses 312 and 314 configured to detachably engage with the end piece unit 20 in the X direction is provided in the engaging section 22. This makes it possible to attach and detach the end piece unit 20 and the multiple recess 312 and 314, for example, in a state where the band section 31 is wrapped around the wrist. Thus, it is possible to mount a variety of the watch head units 10.

In the present embodiment, the recess 313 is provided that suppresses shifting of the end piece unit 20 at least in the X direction when the end piece unit 20 is engaged with the engaging section 22. This makes it possible to suppress unintentional detachment of the end piece unit 20 from the engaging section 22, for example, even in a case where something hits the end piece unit 20.

In the present embodiment, the engaging section 22 is configured to be detachable from the flexible base material 31a. This makes it possible to attach and detach the end piece unit 20 and the engaging section 22, for example, in a state where the band section 31 is wrapped around the wrist. Thus, it is possible to mount a variety of the watch head units 10.

In the present embodiment, the multiple recesses 312 and 314 arranged in the X direction on the outer surface 31a1 are provided in the engaging part 31b of the band section 31; the multiple movable parts 221 and 222 are provided in the end piece unit 20 respectively for the multiple recesses 312 and 314; and the multiple recesses 312 and 314 and the multiple movable parts 221 and 222 are configured to allow the multiple movable parts 221 and 222 to detachably engage with the multiple recesses 312 and 314 in the X direction. This makes it possible to attach and detach the multiple engaging portions 221a and 222a of the end piece unit 20 and the recesses 312 and 314 of the band section 31, for example, in a state where the band section 31 is wrapped around the wrist. Thus, it is possible to mount a variety of the watch head units 10.

In the present embodiment, the recess 313 that accommodates the protrusion 225a is provided at a location corresponding to the protrusion 225a fixed to the casing 225 of the end piece unit 20, in the engaging section 22. This makes it possible to suppress unintentional detachment of the end piece unit 20 from the engaging section 22, for example, even in a case where something hits the end piece unit 20.

In the present embodiment, the end piece unit 20 includes the linking section 21 to be detachably linked to the watch head unit 10, and the engaging section 22 to detachably engage with the band section 31 in a state where the band section 31 is wrapped around the wrist. Thus, for example, by replacing with the end piece unit 20 corresponding to the lug width of the watch head unit 10 to be replaced in a state where the band section 31 is wrapped around the wrist, it is possible to replace with the watch head unit 10 having a different lug width. Thus, it is possible to mount a variety of the watch head units 10.

In the present embodiment, the multiple movable parts 221 and 222 are provided in the end piece unit 20 respectively for the multiple recesses 312 and 314, and the multiple movable parts 221 and 222 are configured to detachably engage with the multiple recesses 312 and 314 in the X direction. This makes it possible to attach and detach the multiple engaging portions 221a and 222a of the end piece unit 20 and the multiple recesses 312 and 314 of the band section 31, for example, in a state where the band section 31 is wrapped around the wrist. Thus, it is possible to mount a variety of the watch head units 10.

In the present embodiment, the protrusion 225a to be accommodated in the recess 313 is provided in the casing 225 of the end piece unit 20. Thus, for example, by accommodating the protrusion 225a in the recess 313, it is possible to suppress unintentional detachment of the end piece unit 20 from the engaging section 22, even in a case where something hits the end piece unit 20.

<2. Modification Examples>

Next, description is given of modification examples of the wristwatch 1 according to the foregoing embodiment.

[Modification Example A]

In the foregoing embodiment, for example, an elastic member 226 may be provided instead of the elastic member 224 as illustrated in FIGS. 10 and 11. FIG. 10 illustrates a modification example of the cross-sectional configuration in FIG. 4. FIG. 11 illustrates a state of displacement of the end piece unit 20 in FIG. 10 at the time when the end piece unit 20 is pressed from both sides.

The elastic member 226 is configured by, for example, an elastic resin such as silicone rubber, an air bag containing air, or the like. Even in a case where such a configuration is adopted, the elastic member 226 has an action similar to that of the elastic member 224, thus making it possible to obtain effects similar to those of the foregoing embodiment.

[Modification Example B]

In the foregoing embodiment, for example, the elastic member 224 may be omitted, and a pair of an N magnet 231 and an S magnet 232 and a pair of an N magnet 233 and an S magnet 234 may be provided, as illustrated in FIGS. 12 and 13. FIG. 12 illustrates a modification example of the cross-sectional configuration in FIG. 4. FIG. 13 illustrates a state of displacement of the end piece unit 20 in FIG. 10 at the time when the end piece unit 20 is pressed from both sides.

In the pair of the N magnet 231 and the S magnet 232, the N magnet 231 is fixed to the movable part 221, for example, and the S magnet 232 is fixed to the rib 225b with a predetermined gap with respect to the N magnet 231. In the pair of the N magnet 233 and the S magnet 234, the N magnet 233 is fixed to the movable part 222, for example, and the S magnet 234 is fixed to the rib 225c with a predetermined gap with respect to the N magnet 233. Also in a case where such a configuration is adopted, the pair of the N magnet 231 and the S magnet 232 and the pair of the N magnet 233 and the S magnet 234 have actions similar to those of the elastic member 224, thus making it possible to obtain effects similar to those of the foregoing embodiment.

[Modification Example C]

In the foregoing embodiment, for example, a band section 33 may be provided instead of the band section 31 as illustrated in FIGS. 14 and 15. FIG. 14 illustrates a modification example of the perspective configuration of the wristwatch 1. FIG. 15 illustrates a perspective configuration example of the band device 30 at the time when the watch head unit 10 and the end piece unit 20 are removed from the wristwatch 1 in FIG. 14.

In the present modification example, the band section 33 has an annular shape, for example, and forms the hollow part S together with the buckle section 32, as illustrated in FIG. 15. The band section 33 has, for example, a configuration in which multiple recesses 331, 332, and 333 are provided on a surface (an outer surface 33a), of a flexible base material, on side opposite to the side of the hollow part S. One end of the band section 33 is linked to the one end of the buckle section 32, and another end of the band section 33 is linked to the other end of the buckle section 32. The multiple recesses 331, 332, and 333 each correspond to a specific example of an "engaging section" of the present disclosure.

The multiple recesses 331, 332, and 333 are configured to be detachable from the engaging section 22 of the end piece unit 20. The multiple recesses 331, 332, and 333 are arranged in a direction orthogonal to an extending direction (Y direction) of the band section 33 on the outer surface 33a. On the outer surface 33a, the direction orthogonal to the extending direction (Y direction) of the band section 33 corresponds to a width direction (hereinafter, referred to as the "X direction" as appropriate) of the band section 33. The recesses 331 and 333 each correspond to a specific example of the "recess" or the "first recess" of the present disclosure. The recess 332 corresponds to a specific example of the "shift suppressing section" or the "second recess" of the present disclosure.

Among the multiple recesses 331, 332, and 333 arranged side by side in the width direction (X direction) of the band section 33, the recesses 331 and 333 positioned at both ends are configured to be detachably engaged with the engaging section 22 of the end piece unit 20 in the width direction (X direction) of the band section 33. The recess 331 is provided to be adjacent to a left end edge of the band section 33 in the width direction (X direction). The recess 333 is provided to be adjacent to a right end edge of the band section 33 in the width direction (X direction). The left end edge of the band section 33 in the width direction (X direction) refers to an end edge of the band section 33, positioned on the left side of time displayed on the display section 11. The right end edge of the band section 33 in the width direction (X direction) refers to an end edge of the band section 33, positioned on the right side of time displayed on the display section 11.

The recess 331 has, for example, a depression 331a projecting toward the left end edge of the band section 33 in the width direction (X direction) as illustrated in FIG. 16. The engaging portion 221a engages with this depression 331a. FIG. 16 illustrates a cross-sectional configuration example as the wristwatch 1 according to the present modification example is taken along the end piece unit 20. The recess 333 has, for example, a depression 333a projecting toward a right end edge of the band section 33 in the width direction (X direction) as illustrated in FIG. 16. The engaging portion 222a engages with this depression 333a. The recess 332 suppresses shifting of the end piece unit 20 at least in the X direction of the X direction and the Y direction at the time when the engaging portions 221a and 222a of the end piece unit 20 engage with the recesses 331 and 333. The protrusion 225a is inserted into the recess 332. When the protrusion 225a is inserted into the recess 332, the recess 332 surrounds side surfaces of the protrusion 225a from four sides with a predetermined gap interposed therebetween. When the protrusion 225a is inserted into the recess 332, the recess 332 may be in contact with at least two side surfaces, of the side surfaces of the protrusion 225a, opposed to each other in the X direction. This suppresses shifting of the end piece unit 20 at least in the X direction of the X direction and the Y direction.

FIG. 17 illustrates a state of displacement of the end piece unit 20 at the time when the movable parts 221 and 222 of the engaging section 22 are pressed from both sides. As illustrated in FIG. 17, pressing the movable parts 221 and 222 from the both sides causes the engaging portion 221a of the movable part 221 to be disengaged from the depression 331a of the recess 331 and causes the engaging portion 222a of the movable part 222 to be disengaged from the depression 333a of the recess 333. This enables the end piece unit 20 to be disengaged from the band section 33 in a state where the band section 33 is wrapped around the wrist. Meanwhile, canceling the pressing on the movable parts 221 and 222 allows the engaging portion 221a of the movable part 221 to engage with the depression 331a of the recess 331, and allows the engaging portion 222a of the movable part 222 to engage with the depression 333a of the recess 333, as illustrated in FIG. 16. This enables the end piece unit 20 to be fixed to the band section 33 in a state where the band section 33 is wrapped around the wrist. That is, the engaging section 22 is configured to make detachable engagement in a state where the band section 33 is wrapped around the wrist.

In the present modification example, the engaging section 22 of the end piece unit 20 is configured to make detachable engagement in a state where the band section 33 is wrapped around the wrist. Thus, for example, by replacing with the end piece unit 20 corresponding to the lug width of the watch head unit 10 to be replaced in a state where the band section 33 is wrapped around the wrist, it is possible to replace with the watch head unit 10 having a different lug width. Thus, it is possible to mount a variety of the watch head units 10.

In the present modification example, the engaging section (multiple recesses 331 and 333) is formed on the outer surface 31a1, of the band section 33, on the side opposite to the side of the hollow part S. This makes it possible to attach and detach the end piece unit 20 and the band section 33 via the engaging section (multiple recesses 331 and 333), for example, in a state where the band section 33 is wrapped around the wrist. Thus, it is possible to mount a variety of the watch head units 10.

In the present modification example, the recess 332 is provided that suppresses shifting of the end piece unit 20 at least in the X direction at the time when the end piece unit 20 is engaged with the engaging section (multiple recesses 331 and 333). This makes it possible to suppress unintentional detachment of the end piece unit 20 from the engaging section (multiple recesses 331 and 333), for example, even in a case where something hits the end piece unit 20.

In the present modification example, the multiple recesses 331 and 333 arranged in the X direction on the outer surface 33a are provided in the band section 33; the multiple movable parts 221 and 222 are provided in the end piece unit 20 respectively for the multiple recesses 331 and 333; and the multiple recesses 331 and 333 and the multiple movable parts 221 and 222 are configured to allow the multiple movable parts 221 and 222 to detachably engage with the multiple recesses 331 and 333 in the X direction. This makes it possible to attach and detach the multiple engaging portions 221a and 222a of the end piece unit 20 and the recesses 331 and 333 of the band section 31, for example, in a state where the band section 33 is wrapped around the wrist. Thus, it is possible to mount a variety of the watch head units 10.

In the present modification example, the recess 332 that accommodates the protrusion 225a is provided at a location corresponding to the protrusion 225a fixed to the casing 225 of the end piece unit 20, in the band section 33. This makes it possible to suppress unintentional detachment of the end piece unit 20 from the band section 33, for example, even in a case where something hits the end piece unit 20.

[Modification Example D]

In the foregoing embodiment and modification examples thereof, the linking section 21 may include, for example, movable parts 215 and 216 to be detachably linked to the watch head unit 10 and an adjusting part 217 that is able to adjust a width of the linking section 21 (movable parts 215 and 216) to a width corresponding to a rim width of the watch head unit 10, as illustrated in FIGS. 18 and 19. The movable part 215 includes a screw portion 215a and the pin 211, and the movable part 216 includes a screw portion 216a and the pin 212. The screw portions 215a and 216a are each a female screw, for example. The movable part 215 is provided at the left end of the linking section 21 in the width direction, and the movable part 216 is provided at the right end of the linking section 21 in the width direction. A predetermined gap is provided between the movable part 215 and the movable part 216.

The adjusting part 217 includes, for example, a screw portion 217c that fits into the screw portion 215a and a screw portion 217d that fits into the screw portion 216a. The screw portions 217c and 217d are each a male screw, for example. The screw portions 215a, 216a, 217c, and 217d are configured to allow, when the screw portions 215a and 216a are rotated by rotation of the screw portions 217c and 217d, a distance between the movable parts 215 and 216 to be displaced. For example, in a case where the screw portion 215a is a right screw and the screw portion 216a is a left screw, the screw portion 217c is a right screw similarly to the screw portion 215a, and the screw portion 217d is a left screw similarly to the screw portion 216a. The adjusting part 217 further includes, for example, a rotary portion 217a having on a front surface thereof unevenness that assists manual rotation of the adjusting part 217, and a rotary portion 217b linked to the rotary portion 217a and having the screw portions 217c and 217d on the end thereof. The screw portion 217c is provided at the left end of the rotary portion 217b, and the screw portion 217d is provided at the right end of the rotary portion 217b.

The linking section 21 further includes, for example, a casing 214 that accommodates the movable parts 215 and 216 and the adjusting part 217 as illustrated in FIGS. 18 and 19. The casing 214 includes an opening 214a that exposes a portion (rotary portion 217a) of the adjusting part 217, an opening 214b that exposes a portion of the movable part 215, and an opening 214c that exposes a portion of the movable part 216. For example, as illustrated in FIG. 20, manually rotating the rotary portion 217a exposed to the opening 214a in the linking section 21 causes the screw portions 217c and 217d to be rotated, and the movable parts 215 and 216 fitted to the screw portions 217c and 217d are displaced accordingly. As a result, the gap between the movable parts 215 and 216 are widened or narrowed, thereby displacing the width of the linking section 21 (movable parts 215 and 216). The casing 214 further includes, for example, a suppressing part 214d that suppresses displacement of the rotary portion 217a in the width direction of the linking section 21, as illustrated in FIGS. 19 and 20. The suppressing part 214d is formed, for example, to sandwich the rotary portion 217a in the width direction of the linking section 21.

In the present modification example, the end piece unit 20 is provided with the adjusting part 217 that is able to adjust the width of the linking section 21 to a width corresponding to a rim width of the watch head unit 10. Thus, for example, by replacing with the end piece unit 20 corresponding to the lug width of the watch head unit 10 to be replaced in a state where the band sections 31 and 33 are wrapped around the wrist, it is possible to replace with the watch head unit 10 having a different lug width. Thus, it is possible to mount a variety of the watch head units 10.

In the present modification example, the linking section 21 is provided with the movable part 215 including the screw portion 215a, the movable part 216 including the screw portion 216a, and the adjusting part 217 including the screw portions 217c and 217d that fit into the screw portions 215a and 216a. Thus, for example, by adjusting the width of the end piece unit 20 to a width corresponding to the lug width of the watch head unit 10 to be replaced in a state where the band sections 31 and 33 are wrapped around the wrist, it is possible to replace with the watch head unit 10 having a different lug width. Thus, it is possible to mount a variety of the watch head units 10.

In the present modification example, the screw portions 215a, 216a, 217c, and 217d are configured to allow, when the screw portions 215a and 216a are rotated by the rotation of the screw portions 217c and 217d, the distance between the movable parts 215 and 216 to be displaced. Thus, for example, by adjusting the width of the end piece unit 20 to a width corresponding to the lug width of the watch head unit 10 to be replaced in a state where the band sections 31 and 33 are wrapped around the wrist, it is possible to replace with the watch head unit 10 having a different lug width. Thus, it is possible to mount a variety of the watch head units 10.

In the present modification example, the casing 214 that accommodates the movable parts 215 and 216 and the adjusting part 217 includes the opening 214a that exposes a portion (rotary portion 217a) of the adjusting part 217, the opening 214b that exposes a portion of the movable part 215, and the opening 214c that exposes a portion of the movable part 216. Thus, for example, by adjusting the width of the end piece unit 20 to a width corresponding to the lug width of the watch head unit 10 to be replaced in a state where the band sections 31 and 33 are wrapped around the wrist, it is possible to replace with the watch head unit 10 having a different lug width. Thus, it is possible to mount a variety of the watch head units 10.

[Modification Example E]

In the foregoing embodiment and modification examples thereof, the linking section 21 may include, for example, the movable parts 215 and 216 to be detachably linked to the watch head unit 10, and an adjusting part that is able to adjust the width of the linking section 21 (movable parts 215 and 216) to a width corresponding to the rim width of the watch head unit 10, as illustrated in FIGS. 21 and 22. FIG. 21 illustrates a perspective configuration example of the linking section 21. FIG. 22 illustrates an inner configuration example of the linking section 21 in FIG. 21.

The movable part 215 includes a groove 215b extending in a direction (hereinafter, referred to as an "oblique direction") obliquely intersecting the width direction of the linking section 21, and a recess 215c provided at the right end of the movable part 215. A protrusion 218b described later is inserted into the groove 215b. The recess 215c accommodates a protrusion 214e described later. The movable part 216 includes a groove 216b extending in an oblique direction as described above, and a recess 216c provided at the left end of the movable part 216. A protrusion 218c described later is inserted into the groove 216b. The recess 216c accommodates a protrusion 214f described later. The movable part 215 is provided at the left end of the linking section 21 in the width direction, and the movable part 216 is provided at the right end of the linking section 21 in the width direction. A predetermined gap is provided between the movable part 215 and the movable part 216.

The adjusting part includes, for example, a rotational mechanism 218, an elastic member 219, and restricting portions 214h and 214i, as illustrated in FIGS. 21 and 22.

The rotational mechanism 218 includes, for example, the protrusion 218b to be inserted into the groove 215b, the protrusion 218c to be inserted into the groove 216b, and a rotary portion 218a that is fixed to the protrusions 218b and 218c and rotates about a protrusion 214g as a central axis in response to displacement of the protrusions 218b and 218c. The elastic member 219 is an energizing member that energizes the movable parts 215 and 216 in a direction in which the distance between the movable parts 215 and 216 is away from each other. The elastic member 219 is configured by, for example, a spring, an elastic resin such as silicone rubber, or an air bag containing air. The restricting portions 214h and 214i are fixed to the casing 214. The restricting portions 214h and 214i restrict the movable parts 215 and 216 to allow the distance between the movable parts 215 and 216 not to exceed a predetermined magnitude. The restricting portion 214h restricts displacement of the movable part 215 in a left direction. The restricting portion 214i restricts displacement of the movable part 216 in a right direction.

Thus, for example, as illustrated in FIGS. 23 and 24, pressing the movable parts 215 and 216 from both sides causes the protrusion 218b to be displaced inside the groove 215b toward side of the left end of the movable part 215 and causes the protrusion 218c to be displaced inside the groove 216b toward side of the right end of the movable part 216. At this time, the protrusions 218b and 218c are linked to the rotary portion 218a, and are equally displaced inside the grooves 215b and 216b by rotation of the rotary portion 218a about the protrusion 214g as a central axis. Therefore, the movable parts 215 and 216 are displaced equally from each other and in a direction away from each other in the X direction. It is to be noted that FIG. 23 illustrates a state of the displacement of the linking section 21 at the time when the linking section 21 in FIG. 21 is pressed from both sides. FIG. 24 illustrates a state of the displacement of the linking section 21 at the time when the linking section 21 in FIG. 22 is pressed from both sides.

Meanwhile, when the pressing on the movable parts 215 and 216 is canceled, the energizing force of the elastic member 219 causes the protrusion 218b to be displaced inside the groove 215b toward the side of the right end of the movable part 215, and causes the protrusion 218c to be displaced inside the groove 216b toward the side of the left end of the movable part 216. At this time, the protrusions 218b and 218c are linked to the rotary portion 218a, and are equally displaced inside the grooves 215b and 216b by the rotation of the rotary portion 218a about the protrusion 214g as a central axis. Therefore, the movable parts 215 and 216 are displaced equally from each other and in a direction closer to each other in the X direction. It is to be noted that the displacement of the movable parts 215 and 216 are stopped at a position where the distance between the movable parts 215 and 216 is of a predetermined magnitude, at least by the restricting portions 214h and 214i.

In the present modification example, the end piece unit 20 is provided with the elastic member 219 that energizes the movable parts 215 and 216 in a direction in which the distance between the movable parts 215 and 216 is away from each other, and the restricting portions 214h and 214i that restrict the movable parts 215 and 216 to allow the distance between the movable parts 215 and 216 not to exceed a predetermined magnitude. Thus, for example, by adjusting the width of the end piece unit 20 to a width corresponding to the lug width of the watch head unit 10 to be replaced in a state where the band sections 31 and 33 are wrapped around the wrist, it is possible to replace with the watch head unit 10 having a different lug width. Thus, it is possible to mount a variety of the watch head units 10.

In the present modification example, the movable part 215 is provided with the groove 215b extending in the oblique direction as described above, and the movable part 216 is provided with the groove 216b extending in the oblique direction as described above. In the present modification example, there is further provided the rotational mechanism 218 including the protrusion 218b to be inserted into the groove 215b, the protrusion 218c to be inserted into the groove 216b, and the rotary portion 218a that is fixed to the protrusions 218b and 218c and rotates about the protrusion 214g as a central axis in response to displacement of the protrusions 218b and 218c. Thus, when the movable parts 215 and 216 are pressed from both sides or the pressing on the movable parts 215 and 216 is canceled, the movable parts 215 and 216 are displaced equally from each other in the X direction. As a result, when the movable parts 215 and 216 are displaced, it is possible to maintain a position of the casing 214 constantly at a center portion of the linking section 21 in a lateral direction.

[Modification Example F]

In the foregoing embodiment and modification examples thereof, for example, the display section 11 of the watch head unit 10 may include, on a back surface on side opposite to a time display surface, a protrusion 13 having stretchability in a direction orthogonal to the back surface, as illustrated in FIG. 25. The protrusion 13 includes, for example, a base material 13a and an elastic member 13b that energizes the base material 13a in a direction away from the back surface. This allows the protrusion 13 to be compressed by a wrist 100 when the wristwatch 1 is wore on the wrist 100, for example, as illustrated in FIG. 26. As a result, the energizing force of the protrusion 13 generated by the compression causes the watch head unit 10 to be pressed in a direction away from the wrist 100, thus causing the buckle section 32 linked to the watch head unit 10 via the band sections 31 and 33 to be pressed against the wrist 100. At this time, the detection electrode 321 of the pulse sensor 421 is exposed, for example, on a surface, of the buckle section 32, on the side of the hollow part S, and the detection electrode 321 is pressed against the wrist 100. Thus, for example, it is possible to measure a pulse accurately using the pulse sensor 421 as compared with the case where a gap G as illustrated in FIG. 27 may be generated between the detection electrode 321 and the wrist 100.

[Modification Example G]

In the foregoing embodiment and modification examples thereof, for example, the band section 31 may include, at a location facing the watch head unit 10 and on a surface (inner surface) on the side of the hollow part S, the protrusion 13 having stretchability in a direction orthogonal to an inner surface of the band section 31, as illustrated in FIG. 28. This allows the protrusion 13 to be compressed by the wrist 100 when the wristwatch 1 is wore on the wrist 100, for example, as illustrated in FIG. 29. As a result, the energizing force of the protrusion 13 generated by the compression causes the watch head unit 10 to be pressed in a direction away from the wrist 100, thus causing the buckle section 32 linked to the watch head unit 10 via the band sections 31 and 33 to be pressed against the wrist 100. At this time, the detection electrode 321 of the pulse sensor 421 is exposed, for example, on a surface, of the buckle section 32, on the side of the hollow part S, and the detection electrode 321 is pressed against the wrist 100. Thus, for example, it is possible to measure a pulse accurately using the pulse sensor 421 as compared with the case where the gap G as illustrated in FIG. 27 may be generated between the detection electrode 321 and the wrist 100.

<3. Second Embodiment>

FIG. 30 illustrates a perspective configuration example of a wristwatch 2 according to a second embodiment of the present disclosure. The wristwatch 2 includes the watch head unit 10, two end piece units 50, and a band device 60.

(Watch Head Unit 10)

The watch head unit 10 includes the display section 11 and the four lugs 12. The display section 11 has a display surface that displays time. The display section 11 may include a dial face, an hour hand, and a minute hand on the display surface, and may be configured to display time by the hour hand and the minute hand pointing to any position on the dial face. The display section 11 may be configured by a liquid crystal display, and may be configured to display, on the display surface, a screen to indicate time on the liquid crystal display. The screen may be a screen simulating an analog watch, or may be a screen that digitally displays time. The watch head unit 10 may have functions of a smartwatch.

Each lug 12 is linked to the display section 11. Each lug 12 projects along an extending direction of a band section 61 (hereinafter, referred to as the "Y direction" as appropriate) described later. Two lugs 12 of the four lugs 12 extend from the upper side of the display section 11 toward the band section 61 to be provided at positions opposed to each other with the end piece unit 50 interposed therebetween. The remaining two lugs 12 of the four lugs 12 extend from the lower side of the display section 11 toward the band section 61 to be provided at positions opposed to each other with the end piece unit 50 interposed therebetween. Each lug 12 is linked to the end piece unit 50. Each lug 12 has a hole, for example. A pin of the end piece unit 50 is inserted into this hole.

(End Piece Unit 50)

The two end piece units 50 are provided at positions opposed to each other with the watch head unit 10 interposed therebetween. One end piece unit 50 is disposed in an interval portion between the two lugs 12 provided on the upper side of the watch head unit 10, and is linked to the two lugs 12 provided on the upper side of the watch head unit 10. Another end piece unit 50 is disposed in an interval portion between the two lugs 12 provided on the lower side of the watch head unit 10, and is linked to the two lugs 12 provided on the lower side of the watch head unit 10. The two end piece units 50 are further linked to the band device 60.

(Band Device 60)

The band device 60 has an annular shape, for example, as illustrated in FIG. 30, and forms the hollow part S together with the watch head unit 10. The band device 60 includes, for example, two band sections 61 and a blade section 62. Among the two band sections 61, one end of the band section 31 provided on the upper side of the watch head unit 10 is linked to one end of the blade section 62, and, among the two band sections 61, one end of the band section 31 provided on the lower side of the watch head unit 10 is linked to another end of the blade section 62. The circuit substrate 40 is mounted on the blade section 62. The circuit substrate 40 is equipped with a sensor function and a wireless communication function, and the pulse sensor 421 that serves a portion of the sensor function is exposed on an inner surface of the blade section 62. FIG. 30 illustrates a state where the detection electrode 321 of the pulse sensor 421 is exposed on the inner surface of the blade section 62.

Each band section 61 includes multiple segments linked in a row in the Y direction. The multiple segments include, for example, a segment 63 linked to the blade section 62, a segment 64 linked to the segment 63, and a segment 65 linked to the segment 64, as illustrated in FIGS. 30, 31, 32, and 33. FIG. 31 illustrates a perspective configuration example of a portion of the band section 61. FIGS. 32 and 33 each illustrate a cross-sectional configuration example of a portion of the band section 61.

Both ends of the blade section 62 have holes. A pin 63a of the segment 63 is inserted into the holes. A portion (an end 64a) of the segment 64 is accommodated in a recess 63b of the segment 63, and a pin 67 is inserted into a hole provided in each side wall of the recess 63b and a through-hole 641 provided in the end 64a of the segment 64. This allows the segments 63 and 64 to be linked to each other rotatably about the pin 67 as a rotational axis. A portion (a member 65a) of the segment 65 is accommodated in a recess of a segment 66 provided closer to the end piece unit 50, and a pin 68 is inserted into a hole provided in each side wall of the recess of the segment 66 and a through-hole 651 provided in a portion (member 65a) of the segment 65. This allows the segments 65 and 66 to be linked to each other rotatably about the pin 68 as a rotational axis.

The segment 64 has a recess 642 having an opening on side of the segment 65, and a fixing part 643 that is provided inside the recess 642 and fixes an elastic member 654 described later. The segment 65 includes the elastic member 654, a tubular part 65c inserted at least partially into the recess 642, the member 65a having a recess 652 that communicates with the tubular part 65c, and a fixing part 653 that is provided inside the recess 652 and fixes the elastic member 654. The elastic member 654 has both ends fixed by the fixing parts 643 and 653, and is disposed inside a space formed by the recess 642, the tubular part 65c, and the recess 652. The segment 65 may further include a pair of guide parts 65b to guide stretching and contraction of the elastic member 654 together with the tubular part 65c and the recess 642. The pair of guide parts 65b are arranged to sandwich the segment 64.

FIG. 34 illustrates a state of the band section 61 at the time when a portion of the band section 61 is extended. FIGS. 35 and 36 each illustrate a cross-sectional configuration example of a portion of the band section 61 in FIG. 34. As illustrated in FIG. 34, when the segment 65 is pulled to side of the end piece unit 50, the member 65a and the pair of guide parts 65b of the segment 65 are displaced to the side of the end piece unit 50, and the elastic member 654 extends accordingly. At this time, the extension of the elastic member 654 is guided by the tubular part 65c, the recess 642, and the pair of guide parts 65b. In this manner, the length of the band section 61 is adjusted.

In the present embodiment, the length of the band section 61 is adjusted by providing the segments 64 and 65 for each band section 61. This allows the blade section 62 linked to the band section 61 to be pressed against the wrist 100. At this time, the detection electrode 321 of the pulse sensor 421 is exposed, for example, on a surface, of the blade section 62, on the side of the hollow part S, and the detection electrode 321 is pressed against the wrist 100. Thus, for example, it is possible to measure a pulse accurately using the pulse sensor 421 as compared with the case where the gap G as illustrated in FIG. 27 may be generated between the detection electrode 321 and the wrist 100.

<4. Third Embodiment>

FIG. 37 illustrates a perspective configuration example of a wristwatch 3 according to a third embodiment of the present disclosure. The wristwatch 3 includes a watch head unit 70, an end piece unit 80 described later, and a band device 90.

(Watch Head Unit 70)

The watch head unit 70 includes a display section 71. The display section 71 has a display surface that displays time. The display section 71 may include a dial face, an hour hand, and a minute hand on the display surface, and may be configured to display time by the hour hand and the minute hand pointing to any position on the dial face. The display section 71 may be configured by a liquid crystal display, and may be configured to display, on the display surface, a screen to indicate time on the liquid crystal display. The screen may be a screen simulating an analog watch, or may be a screen that digitally displays time. The watch head unit 70 may have functions of a smartwatch.

(Band Device 90)

FIG. 38 illustrates a perspective configuration example of the band device 90 at the time when the watch head unit 70 and the end piece unit 80 are removed from the wristwatch 3. The band device 90 includes, for example, band sections 91 and 92, and the buckle section 32. One end of the band section 91 is linked to one end of the buckle section 32, and one end of the band section 92 is linked to another end of the buckle section 32. Among both ends of the band section 91, an end different from the end linked to the buckle section 32 is an open end. Among both ends of the band section 92, an end different from the end linked to the buckle section 32 is provided with a linking part 92a to be detachably linked to the band section 91. The circuit substrate 40 is mounted on the buckle section 32. The circuit substrate 40 is equipped with a sensor function and a wireless communication function, and the pulse sensor 421 that serves a portion of the sensor function is exposed on an inner surface of the buckle section 32 (an inner surface of the band device 90). FIGS. 37 and 38 each illustrate a state where the detection electrode 321 of the pulse sensor 421 is exposed on the inner surface of the buckle section 32 (inner surface of the band device 90).

The band sections 91 and 92 form the hollow part S together with the buckle section 32. The band sections 91 and 92 are each configured by a flexible base material, for example. The base material to be used in the band sections 91 and 92 is, for example, a flexible sheet base material configured by a resin material such as rubber. The band section 91 includes, for example, an engaging section 93 at least on an end, of a back surface of the base material of the band section 91 (an inner surface of the band section 91 on the side of the hollow part S), on side of the band section 92, as illustrated in FIG. 39. FIG. 39 illustrates a perspective configuration example of a back surface of the wristwatch 3. The engaging section 93 includes a strip-shaped protrusion extending in a direction parallel to an extending direction (Y direction) of the band section 91 on the inner surface of the band section 91 on the side of the hollow part S. This protrusion includes comb-teeth parts 93a and 93b on both side surfaces of the protrusion. The comb-teeth parts 93a and 93b are formed on at least the end, of the back surface of the base material of the band section 91 (inner surface of the band section 91 on the side of the hollow part S), on the side of the band section 92. The comb-teeth part 93a is provided on one side surface of the protrusion, and the comb-teeth part 93b is provided on another side surface of the protrusion.

(End Piece Unit 80)

The end piece unit 80 is provided on a back surface of the watch head unit 70, for example, as illustrated in FIG. 39. The end piece unit 80 may be fixed to the back surface of the watch head unit 70 or may be detachably linked thereto. The end piece unit 80 includes movable sections 80a and 80b opposed to each other with a location facing the protrusion provided on the back surface of the base material of the band section 91 interposed therebetween. The movable section 80*a* is provided on side of the comb-teeth part 93*a*, and the movable section 80*b* is provided on side of the comb-teeth part 93*b*. The protrusion (comb-teeth parts 93*a* and 93*b*) and the movable sections 80*a* and 80*b* provided on the back surface of the base material of the band section 91 are arranged to allow the movable sections 80*a* and 80*b* to detachably engage in the X direction with the protrusion (comb-teeth parts 93*a* and 93*b*) provided on the back surface of the base material of the band section 91.

The movable section 80*a* includes an engaging part 83 that engages with the comb-teeth part 93*a*, and an energizing part 86 that energizes the engaging part 83 toward the comb-teeth part 93*a*. The movable section 80*b* includes an engaging part 84 that engages with the comb-teeth part 93*b*, and an energizing part 85 that energizes the engaging part 84 toward the comb-teeth part 93*b*. The movable section 80*a* includes a linking section 82 that is energized by the energizing part 86 in a direction opposite to the engaging part 83 and is linked to the engaging part 84. The movable section 80*b* includes a linking section 81 that is energized by the energizing part 85 in a direction opposite to the engaging part 84 and is linked to the engaging part 83.

FIG. 40 illustrates a state of displacement of the end piece unit 80 at the time when the movable sections 80*a* and 80*b* are pressed from both sides. As illustrated in FIG. 40, when the movable sections 80*a* and 80*b* are pressed from both sides, the engaging part 83 of the movable section 80*a* is disengaged from the comb-teeth part 93*a*, and the engaging part 84 of the movable section 80*b* is disengaged from the comb-teeth part 93*b*. This enables the end piece unit 20 to be removed from the band section 31 in a state where the band sections 91 and 92 are wrapped around the wrist. Meanwhile, when the pressing on the movable sections 80*a* and 80*b* is canceled, the engaging part 83 of the movable section 80*a* engages with the comb-teeth part 93*a*, and the engaging part 84 of the movable section 80*b* engages with the comb-teeth part 93*b*, as illustrated in FIG. 39. This enables the watch head unit 70 to be fixed to the band device 90 in a state where the band sections 91 and 92 are wrapped around the wrist. That is, the movable sections 80*a* and 80*b* are configured to make detachable engagement in a state where the band sections 91 and 92 are wrapped around the wrist.

In the present embodiment, the movable sections 80*a* and 80*b* of the end piece unit 80 are configured to make detachable engagement in a state where the band sections 91 and 92 are wrapped around the wrist. Thus, for example, by replacing with the watch head unit 70 together with the end piece unit 80 in a state where the band sections 91 and 92 are wrapped around the wrist, it is possible to replace with the watch head unit 70 having a different lug width. Thus, it is possible to mount a variety of the watch head units 70.

In the present embodiment, the movable sections 80*a* and 80*b* of the end piece unit 80 are formed on the inner surface of the band section 91 on the side of the hollow part S. Here, the protrusion (comb-teeth parts 93*a* and 93*b*) and the movable sections 80*a* and 80*b* provided on the inner surface of the band section 91 on the side of the hollow part S are configured to allow the movable sections 80*a* and 80*b* to detachably engage in the X direction with the protrusion (comb-teeth parts 93*a* and 93*b*) provided on the back surface of the base material of the band section 91. This enables the end piece unit 80 and the band section 91 to be attached and detached via the protrusion (comb-teeth parts 93*a* and 93*b*) and the movable sections 80*a* and 80*b*, for example, in a state where the band section 31 is wrapped around the wrist. Thus, it is possible to mount a variety of the watch head units 70.

Although the description has been given hereinabove of the present disclosure with reference to the multiple embodiments and the multiple modification examples, the present disclosure is not limited to the above-described embodiments, etc., and may be modified in a wide variety of ways. It is to be noted that the effects described herein are merely illustrative. The effects of the present disclosure are not limited to those described herein. The present disclosure may include other effects than those described herein.

In addition, for example, the present disclosure may include the following configurations.

(1)

A band device including:

a sensor unit; and a band unit that is linked to the sensor unit and forms a hollow part together with the sensor unit, in which the band unit includes an end piece section to which a watch head section is attached, and an engaging section that makes detachable engagement in a state where the band unit is wrapped around a wrist.

(2)

The band device according to (1), in which the engaging section is formed on an inner surface of the band unit on side of the hollow part or on an outer surface thereof on side opposite to the side of the hollow part.

(3)

The band device according to (2), in which the engaging section has multiple recesses that are arranged in a first direction orthogonal to an extending direction of the band unit on the outer surface and are configured to detachably engage with the end piece section in the first direction.

(4)

The band device according to (3), in which the band unit further includes a shift suppressing section that suppresses shifting of the end piece section at least in the first directions when the end piece section is engaged with the engaging section.

(5)

The band device according to (3) or (4), in which the band unit further includes a flexible base material, and the engaging section is configured to be detachable from the base material.

(6)

The band device according to (3) or (4), in which the band unit further includes a flexible base material, and the engaging section is formed in the base material.

(7)

The band device according to (2), in which the engaging section includes a strip-shaped protrusion extending in a second direction parallel to an extending direction of the band unit on the inner surface, and the protrusion includes a comb-teeth section on both side surfaces of the protrusion.

(8)

A wristwatch including:

a sensor unit;

a band unit that is linked to the sensor unit and forms a hollow part together with the sensor unit;

an end piece section that is detachably linked to the band unit; and a watch head section that is detachably linked to the end piece section, in which the band unit includes the end piece section to which the watch head section is attached, and an engaging section that makes detachable engagement in a state where the band unit is wrapped around a wrist.

(9)
The wristwatch according to (8), in which the engaging section is formed on an inner surface of the band unit on side of the hollow part or on an outer surface thereof on side opposite to the side of the hollow part.

(10)
The wristwatch according to (9), in which
the engaging section has multiple first recesses arranged in a first direction orthogonal to an extending direction of the band unit on the outer surface,
the end piece section includes multiple movable parts provided one by one for the respective first recesses, and
the multiple first recesses and the multiple movable parts are configured to allow the multiple movable parts to detachably engage with the multiple first recesses in the first direction.

(11)
The wristwatch according to (10), in which
the end piece section includes a casing that accommodates the multiple movable parts, and a protrusion fixed to the casing, and
the band unit includes a second recess that accommodates the protrusion at a location corresponding to the protrusion.

(12)
The wristwatch according to (9), in which
the engaging section includes a strip-shaped protrusion extending in a second direction parallel to an extending direction of the band unit on the inner surface,
the end piece section includes a first movable part and a second movable part opposed to each other with a location facing the protrusion interposed therebetween, and
the protrusion, the first movable part, and the second movable part are configured to allow the first movable part and the second movable part to detachably engage with the protrusion in the first direction.

(13)
The wristwatch according to (12), in which
the protrusion includes a first comb-teeth portion provided on one side surface of the protrusion, and a second saw-teeth portion on another side surface of the protrusion,
the first movable part includes a first engaging portion that engages with the first saw-teeth portion, and a first energizing portion that energizes the first engaging portion toward the first saw-teeth portion,
the second movable part includes a second engaging portion that engages with the second saw-teeth portion, and a second energizing portion that energizes the second engaging portion toward the second saw-teeth portion,
the first movable part includes a first linking portion that is energized by the first energizing portion in a direction opposite to the first engaging portion and is linked to the second engaging portion, and
the second movable part includes a second linking portion that is energized by the second energizing portion in a direction opposite to the second engaging portion and is linked to the first engaging portion.

(14)
An end piece including:
a linking section that is detachably linked to a watch head section; and
an engaging section that detachably engages with a band unit in a state where the band unit is wrapped around a wrist.

(15)
The end piece according to (14), in which
the engaging section includes multiple movable parts, and
in a case where the band unit has multiple recesses arranged in a first direction orthogonal to an extending direction of the band unit, the multiple movable parts are configured to detachably engage with the multiple recesses in the first direction.

(16)
The end piece according to (15), further including, in a case where the band unit has a recess, a protrusion that is inserted into the recess.

(17)
An end piece including:
a linking section that is detachably linked to a watch head section; and
an adjusting part that is able to adjust a width of the linking section to a width corresponding to a rim width of the watch head section.

(18)
The end piece according to (17), in which
the linking section includes a first movable part including a first screw portion and a second movable part including a second screw portion, and
the adjusting part includes a third screw portion that fits into the first screw portion and the second screw portion.

(19)
The end piece according to (18), in which the first screw portion and the second screw portion are configured to allow a distance between the first movable part and the second movable part to be displaced when the first screw portion and the second screw portion are rotated by rotation of the third screw portion.

(20)
The end piece according to (19) further including a casing that accommodates the linking section and the adjusting part, in which
the casing has a first opening that exposes a portion of the adjusting part, a second opening that exposes a portion of the first movable part, and a third opening that exposes a portion of the second movable part.

(21)
The end piece according to (17), in which
the linking section includes a first movable part and a second movable part, and
the adjusting part includes an energizing portion that energizes the first movable part and the second movable part to allow a distance between the first movable part and the second movable part to be away from each other, and a restricting portion that restricts the first movable part and the second movable part to allow the distance not to exceed a predetermined magnitude.

(22)
The end piece according to (21), in which
the first movable part has a first groove extending in a first direction obliquely intersecting a width direction of the linking section,
the second movable part has a second groove extending in the first direction, and the adjusting part includes a first protrusion that is inserted into the first groove, a second protrusion that is inserted into the second groove, and a rotary portion that is fixed to the first protrusion and the second protrusion and rotates in response to displacement of the first protrusion and the second protrusion.

(23)

A wristwatch including:

a sensor unit;

a band unit that is linked to the sensor unit and forms a hollow part together with the sensor unit;

an end piece section that is detachably linked to the band unit; and a watch head section that is detachably linked to the end piece section, the end piece section including a linking section that is detachably linked to the watch head section, and an adjusting part that is able to adjust a width of the linking section to a width corresponding to a rim width of the watch head section.

(24)

A watch head including:

a display part that displays time; and multiple lugs linked to the display part, in which the display part includes, on a back surface on side opposite to a time display surface, a protrusion that is stretchable in a direction orthogonal to the back surface.

(25)

The watch head according to (24), in which the protrusion includes a base material, and an elastic member that energizes the base material in a direction away from the back surface.

(26)

A wristwatch including:

a watch head section;

a sensor unit;

an end piece section that is detachably linked to the watch head section; and a band unit that is linked to the sensor unit and is detachably linked to the watch head section, the band unit forming a hollow part together with the sensor unit, the watch head section including a display part that displays time, and multiple lugs linked to the display part, the display part including, on a back surface on side opposite to a time display surface, a protrusion that is stretchable in a direction orthogonal to the back surface.

(27)

A band device including:

a sensor unit; and a band unit that is linked to the sensor unit and forms a hollow part together with the sensor unit, in which the band unit includes, on an inner surface of the band unit on side of the hollow part, a protrusion that is stretchable in a direction orthogonal to the inner surface.

(28)

The band device according to (27), in which the protrusion includes a base material, and an elastic member that energizes the base material in a direction away from the inner surface.

(29)

A wristwatch including:

a watch head section;

a sensor unit;

an end piece section that is detachably linked to the watch head section; and a band unit that is linked to the sensor unit and is detachably linked to the watch head section, the band unit forming a hollow part together with the sensor unit, in which the band unit includes, on an inner surface of the band unit on side of the hollow part, a protrusion that is stretchable in a direction orthogonal to the inner surface.

(30)

The wristwatch according to claim 13, in which the protrusion includes a base material, and an elastic member that energizes the base material in a direction away from the inner surface.

(31)

A band device including:

a sensor unit; and a band unit that is linked to the sensor unit and forms a hollow part together with the sensor unit, in which the band unit includes a first segment and a second segment linked to each other by an elastic member.

(32)

The band device according to (31), in which the first segment includes a first recess having an opening on side of the second segment, and a first fixing part that is provided inside the first recess and fixes the elastic member, the second segment includes a tubular part inserted at least partially into the first recess, a second recess that communicates with the tubular part, and a second fixing part that is provided inside the second recess and fixes the elastic member, and the elastic member has both ends fixed by the first fixing part and the second fixing part, and is disposed inside a space formed by the first recess, the tubular part, and the second recess.

(33)

The band device according to (32), in which the second segment further includes a guide part that guides stretching and contraction of the elastic member together with the tubular part.

(34)

A wristwatch including:

a sensor unit;

a band unit that is linked to the sensor unit and forms a hollow part together with the sensor unit;

an end piece section that is detachably linked to the band unit; and a watch head section that is detachably linked to the end piece section, in which the band unit includes a first segment and a second segment linked to each other by an elastic member.

This application claims the benefit of Japanese Priority Patent Application JP2020-013153 filed with the Japan Patent Office on Jan. 30, 2020, the entire contents of which are incorporated herein by reference.

It should be understood by those skilled in the art that various modifications, combinations, sub-combinations, and alterations may occur depending on design requirements and other factors insofar as they are within the scope of the appended claims or the equivalents thereof.

The invention claimed is:

1. A band device, comprising:

a sensor unit; and a band unit linked to the sensor unit, wherein the band unit form a hollow part together with the sensor unit, and the band unit includes:
an end piece section to which a watch head section is attached, and
an engaging section configured to make detachable engagement in a state where the band unit is wrapped around a wrist, wherein
the engaging section is on one of an inner surface of the band unit on a side of the hollow part or an outer surface of the band unit on a side opposite to the side of the hollow part,
the engaging section includes a strip-shaped protrusion that extends in a first direction parallel to an extending direction of the band unit on the inner surface, and
the strip-shaped protrusion includes a comb-teeth portion on both side surfaces of the strip-shaped protrusion.

2. The band device according to claim 1, wherein
the engaging section has multiple recesses arranged in a second direction orthogonal to the extending direction of the band unit on the outer surface, and
the multiple recesses are configured to detachably engage with the end piece section in the second direction.

3. The band device according to claim 2, wherein
the band unit further includes a shift suppressing section, and
the shift suppressing section is configured to suppress a shifting operation of the end piece section at least in the second direction based on the end piece section is engaged with the engaging section.

4. The band device according to claim 2, wherein
the band unit further includes a flexible base material, and
the engaging section is configured to be detachable from the flexible base material.

5. The band device according to claim 2, wherein
the band unit further includes a flexible base material, and
the engaging section is in the flexible base material.

6. A wristwatch, comprising:
a sensor unit; and
a band unit linked to the sensor unit, wherein the band unit form a hollow part together with the sensor unit, wherein the band unit includes:
an end piece section to which a watch head section is detachably attached, and
an engaging section configured to make detachable engagement in a state where the band unit is wrapped around a wrist, wherein
the engaging section is on one of an inner surface of the band unit on a side of the hollow part or an outer surface of the band unit on a side opposite to the side of the hollow part,
the engaging section includes a strip-shaped protrusion that extends in a first direction parallel to an extending direction of the band unit on the inner surface, and
the strip-shaped protrusion includes a comb-teeth portion on both side surfaces of the strip-shaped protrusion.

7. The wristwatch according to claim 6, wherein
the engaging section has multiple first recesses arranged in a second direction orthogonal to the extending direction of the band unit on the outer surface,
the end piece section includes multiple movable parts, wherein each movable part of the multiple movable parts is for a respective recess of the multiple first recesses, and
the multiple first recesses and the multiple movable parts are configured to allow the multiple movable parts to detachably engage with the multiple first recesses in the second direction.

8. The wristwatch according to claim 7, wherein the end piece section includes:
a casing, wherein the casing is configured to accommodate the multiple movable parts, and
a protrusion fixed to the casing, and
the band unit has a second recess, wherein the second recess that accommodates the protrusion at a location corresponding to the protrusion.

9. The wristwatch according to claim 6, wherein
the end piece section includes a first movable part and a second movable part opposed to each other with a location, facing the strip-shaped protrusion, interposed therebetween, and
the first movable part and the second movable part are configured to detachably engage with the strip-shaped protrusion in a second direction orthogonal to the extending direction.

10. The wristwatch according to claim 9, wherein
the strip-shaped protrusion includes a first comb-teeth portion on one side surface of the strip-shaped protrusion, and a second comb-teeth portion on another side surface of the strip-shaped protrusion,
the first movable part includes;
a first engaging portion configured to engage with the first comb-teeth portion, and
a first energizing portion configured to the first engaging portion toward the first comb-teeth portion,
the second movable part includes:
a second engaging portion configured to engage with the second comb-teeth portion, and
a second energizing portion configured to energize the second engaging portion toward the second comb-teeth portion,
the first movable part includes a first linking portion, wherein
the first linking portion is energized by the first energizing portion in a direction opposite to the first engaging portion, and
the first linking portion is linked to the second engaging portion, and the second movable part includes a second linking portion, wherein
the second linking portion is energized by the second energizing portion in a direction opposite to the second engaging portion, and
the second linking portion is linked to the first engaging portion.

11. An end piece, comprising:
a linking section configured to detachably linked to a watch head section; and
an engaging section configured to detachably engaged with a band unit in a state where the band unit is wrapped around a wrist, wherein
the engaging section is on one of an inner surface of the band unit on a side of a hollow part of the band unit or an outer surface of the band unit on a side opposite to the side of the hollow part,
the engaging section includes a strip-shaped protrusion that extends in a first direction parallel to an extending direction of the band unit on the inner surface, and
the strip-shaped protrusion includes a comb-teeth portion on both side surfaces of the strip-shaped protrusion.

12. The end piece according to claim 11, wherein
the engaging section includes multiple movable parts,
the band unit comprises multiple recesses arranged in a second direction orthogonal to the extending direction of the band unit, and
the multiple movable parts are configured to detachably engage with the multiple recesses in the second direction.

13. The end piece according to claim 12, further comprising
a protrusion inserted into a recess of the multiple recesses.

\* \* \* \* \*